(12) United States Patent
Morinaga et al.

(10) Patent No.: US 7,512,501 B2
(45) Date of Patent: Mar. 31, 2009

(54) DEFECT INSPECTING APPARATUS FOR SEMICONDUCTOR WAFER

(75) Inventors: Hiroyuki Morinaga, Yokohama (JP); Atsushi Onishi, Yokkaichi (JP); Masayoshi Yamasaki, Oita (JP); Takema Ito, Yokohama (JP); Yasuhiro Kaga, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/889,765

(22) Filed: Aug. 16, 2007

(65) Prior Publication Data

US 2008/0052021 A1 Feb. 28, 2008

(30) Foreign Application Priority Data

Aug. 22, 2006 (JP) .............................. 2006-225284

(51) Int. Cl.
*G01B 5/28* (2006.01)
*G01B 5/30* (2006.01)

(52) U.S. Cl. ............................ 702/35; 702/81; 702/117; 702/189; 257/E21.53; 438/6; 438/48

(58) Field of Classification Search .................... 702/35, 702/81, 84, 117, 189; 257/E21.53; 438/6, 438/11, 48; 250/307, 310; 382/141; 324/501, 324/702, 751
See application file for complete search history.

(56) References Cited

U.S. PATENT DOCUMENTS 5,465,145 A * 11/1995 Nakashige et al. ......... 356/237.5
6,483,937 B1 * 11/2002 Samuels ..................... 382/144
6,906,794 B2 * 6/2005 Tsuji ......................... 356/237.4
7,332,359 B2 * 2/2008 Hamamatsu et al. .......... 438/14
2002/0113234 A1 8/2002 Okuda et al.

FOREIGN PATENT DOCUMENTS

JP 2002-323458 11/2002

* cited by examiner

*Primary Examiner*—Edward Raymond
*Assistant Examiner*—Elias Desta
(74) *Attorney, Agent, or Firm*—Finnegan, Henderson, Farabow, Garrett & Dunner, L.L.P.

(57) ABSTRACT

A defect inspecting apparatus comprising:
an inspection region dividing section which divides a defect inspection region of a wafer on which a circuit pattern is formed into a plurality of inspection subregions;
a pattern density calculating section which calculates the pattern density of each of the inspection subregions on the basis of design data of the circuit pattern;
an inspection execution region and sensitivity rank setting section which assigns a sensitivity rank based on the pattern density to a plurality of inspection execution regions, each including a plurality of the inspection subregions; and
a defect inspecting section which sets an inspection parameter on the basis of sensitivity ranks of the inspection execution regions and inspects the inspection execution regions for a defect.

20 Claims, 20 Drawing Sheets

| MAXIMUM COVERAGE | 0.9 |
|---|---|
| MAXIMUM EDGE DENSITY | 0.22 |

| COVERAGE | EDGE DENSITY | EVALUATED VALUE |
|---|---|---|
| ... | | |
| 0.32 | 0.11 | 0.0638 |
| 0.73 | 0.15 | 0.0119 |
| 0.69 | 0.17 | 0.0105 |
| 0 | 0 | 0.198 |
| 0.51 | 0.15 | 0.0273 |
| 0.71 | 0.19 | 0.0057 |
| ... | | |

DEFECT INSPECTING APPARATUS FOR SEMICONDUCTOR WAFER

CROSS REFERENCE TO RELATED APPLICATIONS

This application is based upon and claims benefit of priority under 35 USC 119 from Japanese Patent Application No. 2006-225284, filed on Aug. 22, 2006, the entire contents of which are incorporated herein by reference.

BACKGROUND OF THE INVENTION

The present invention relates to a defect inspecting apparatus, a defect inspecting method, a semiconductor device manufacturing system, and a semiconductor device manufacturing method.

In a semiconductor device manufacturing process, many patterned elements are formed in multiple layers on a semiconductor wafer. Electric properties of completed elements are inspected and defective elements are excluded from the assembly process. Yields are very important in the semiconductor device manufacturing process. The results of the inspection of the electric properties are fed back to the manufacturing process and are used for managing each process step. However, the semiconductor device manufacturing process involves many process steps and takes a considerably long time from the start of the manufacturing to the inspection of the electric properties. Therefore, when a defect is found by an inspection of electric properties during the manufacturing process, many wafers have already been in process at that point in time and the result of the inspection cannot adequately be used for improving yields.

Therefore, patterns formed in a process step (for example in each layer) are inspected for defects (such as contaminations and pattern defects). By conducting inspections in multiple process steps in the manufacturing process, defects can be quickly detected and the result of the inspection can be quickly reflected in process control.

A defect inspection is performed by illuminating a wafer with inspection light, collecting reflected light with a lens, generating an image with an image sensor, and comparing the image with a reference image. The intensity of reflected inspection light varies depending on patterns on the wafer. Accordingly, if the same level of light is used and the same threshold of the intensity of received light above which an element is regarded as a defective one is set, regions (high-sensitivity regions) where defects can be readily detected and regions (low-sensitivity regions) where defects cannot readily be detected appear. To address this, in the case of a memory product which has a cell section of a simple shape and includes a small number of cells, an operator conducts defect inspections of the memory product by manually setting different sensitivities for the cell section and the surrounding circuit section while watching the wafer.

However, in the case of a product such as a logic product which has random patterns, it is difficult to manually setting sensitivities because many high-sensitivity regions and low-sensitivity regions are scattered. Therefore, in the case of a logic product, the entire wafer must be inspected with the same sensitivity and, once the false defect rate has been reduced to a certain value, defects in low-sensitivity regions cannot be detected.

To solve the problem, a defect inspecting apparatus has been proposed in which a region to be inspected is divided into inspection subregions, the line density (=area of line/area of inspection subregion) of each inspection subregion is calculated, a sensitivity rank is assigned to the region on the basis of the calculated line density, and an inspection parameter is set (see Japanese Patent Laid-Open No. 2002-323458, for example).

However, a sensitivity rank based only on the line density does not agree with an actual defect detection sensitivity. Furthermore, the number of inspection subregions to which sensitivity ranks are assigned is enormous. When they are directly provided to the inspecting apparatus, it has been possible that the inspecting apparatus cannot properly function or inspection regions cannot successfully be set.

SUMMARY OF THE INVENTION

According to one aspect of the present invention, there is provided a defect inspecting apparatus comprising:
an inspection region dividing section which divides a defect inspection region of a wafer on which a circuit pattern is formed into a plurality of inspection subregions;
a pattern density calculating section which calculates the pattern density of each of the inspection subregions on the basis of design data of the circuit pattern;
an inspection execution region and sensitivity rank setting section which assigns a sensitivity rank based on the pattern density to a plurality of inspection execution regions, each including a plurality of the inspection subregions; and
a defect inspecting section which sets an inspection parameter on the basis of sensitivity ranks of the inspection execution regions and inspects the inspection execution regions for a defect.

According to one aspect of the present invention, there is provided a defect inspecting method comprising:
dividing a defect inspection region of a wafer on which a circuit pattern is formed into a plurality of inspection subregions;
calculating the pattern density of each of the inspection subregions on the basis of design data of the circuit pattern;
assigning a sensitivity rank based on the pattern density to a plurality of inspection execution regions, each including a plurality of the inspection subregions; and
setting an inspection parameter on the basis of sensitivity ranks of the inspection execution regions and inspecting the inspection execution regions for a defect.

According to one aspect of the present invention, there is provided a semiconductor apparatus manufacturing system comprising:
a patterning apparatus which forms a circuit pattern on a wafer in accordance with an equipment parameter;
a defect inspecting apparatus comprising an inspection region dividing section which divides a defect inspection region of the wafer on which the circuit pattern is formed into a plurality of inspection subregions, a pattern density calculating section which calculates the pattern density of each of the inspection subregions on the basis of design data of the circuit pattern, an inspection execution region and sensitivity rank setting section which assigns a sensitivity rank based on the pattern density to a plurality of inspection execution regions, each including a plurality of the inspection subregions, and a defect inspecting section which sets an inspection parameter on the basis of sensitivity ranks of the inspection execution regions, inspects the inspection execution regions for a defect, and outputs the result of the inspection; and
an equipment parameter controller which generates correction information for the equipment parameter on the basis of the result of the inspection and outputs the correction information to the patterning apparatus.

According to one aspect of the present invention, there is provided a semiconductor apparatus manufacturing method comprising:

forming a circuit pattern on a wafer in accordance with an equipment parameter;

dividing a defect inspection region of the wafer on which the circuit pattern is formed into a plurality of inspection subregions;

calculating the pattern density of each of the inspection subregions on the basis of design data of the circuit pattern;

assigning a sensitivity rank based on the pattern density to a plurality of inspection execution regions, each including a plurality of the inspection subregions;

setting an inspection parameter on the basis of sensitivity ranks of the inspection execution regions and performing defect inspection on the inspection execution regions;

correcting the equipment parameter on the basis of the result of the defect inspection; and forming a circuit pattern on a wafer in accordance with the corrected equipment parameter.

DETAILED DESCRIPTION OF THE INVENTION

Embodiments of the present invention will be described below with reference to the accompanying drawings.

FIRST EMBODIMENT

Figure 1:
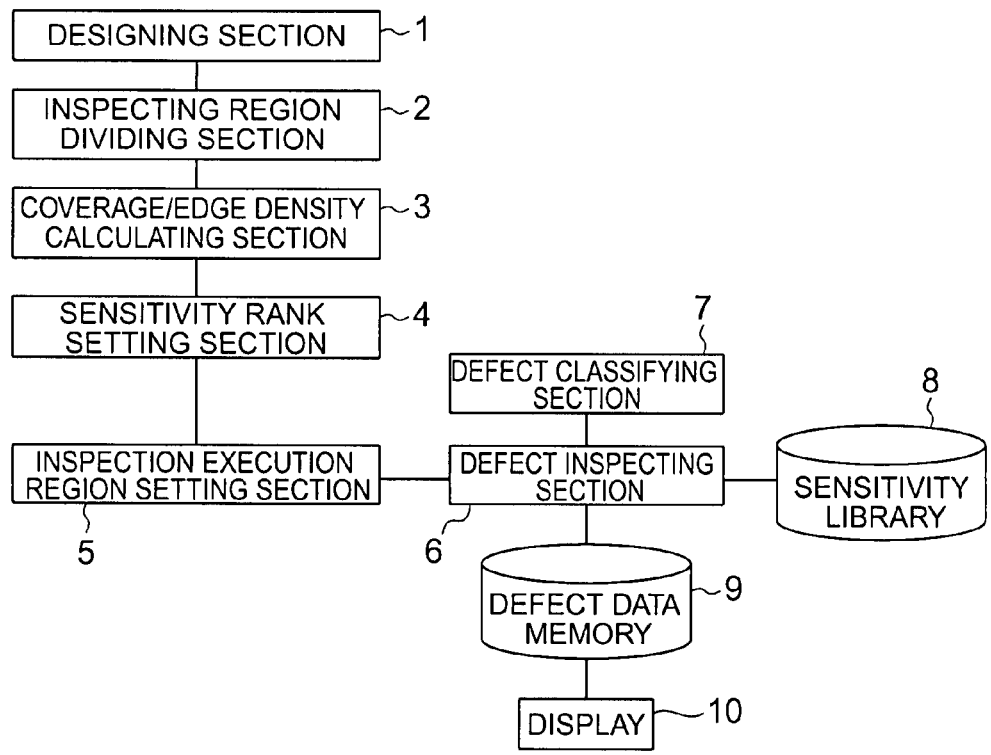
FIG. 1 is a diagram schematically showing a configuration of a defect inspecting apparatus according to a first embodiment of the present invention.

FIG. 1 schematically shows a configuration of a defect inspecting apparatus according to a first embodiment of the present invention. Design data (mask data) is output from a designing section 1. An inspection region dividing section 2 divides an inspection region of a chip to be inspected into subregions. A coverage/edge density calculating section 3 calculates the coverage and edge density of each of the inspection subregions. Based on the calculated coverages and edge densities, a sensitivity rank setting section 4 calculates evaluated sensitivity values of the inspection subregions and sets sensitivity ranks on the basis of the evaluated sensitivity. An inspection execution region setting section 5 groups the inspection subregions to which the same sensitivity rank is assigned together, applies graphics processing to the grouped inspection subregions so that the shape of the grouped inspection subregions becomes rectangular, thereby setting an inspection execution region. This is done in order to sets a rectangular inspection region when an inspection is conducted in a defect inspecting section 6. In the defect inspecting section 6, an inspection parameter (such as a light level or a received light intensity threshold) is set for each sensitivity rank.

The defect inspecting section 6 performs a defect inspection and a defect classifying section 7 classifies detected defects by their causes and sets an inspection parameter such that a false defect rate less than a predetermined value is achieved. After the inspection parameter is set, a typical evaluated sensitivity value (typical evaluated value) in the inspection execution region and the set inspection parameter are stored in a sensitivity library 8. The typical evaluation value may be the median or average value, for example, of evaluated sensitivity values in the inspection execution region. In the subsequent defect inspections, the typical evaluated value is used to search the sensitivity library 8 to retrieve the inspection parameter. Thus, the setting of inspection parameters can be automated. Detected defects are stored in a defect data memory 9 and are displayed in a wafer map or a chart on a display 10.

Operations of these sections will be described below.

Figure 2:
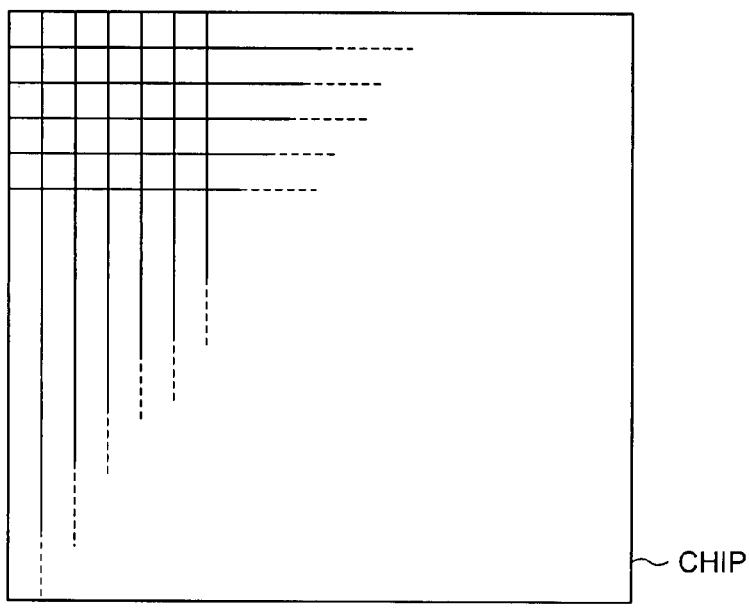
FIG. 2 is a diagram showing exemplary division of an inspection region in the defect inspecting apparatus.

The inspection region dividing section 2 divides a region to be inspected of a chip under inspection into multiple subregions. For example, the region is divided into subregions in a grid pattern as shown in FIG. 2. The size of each cell of the grid may be arbitrarily set. It is assumed in the following description that the region to be inspected has been divided into subregions in a grid.

Figure 3:
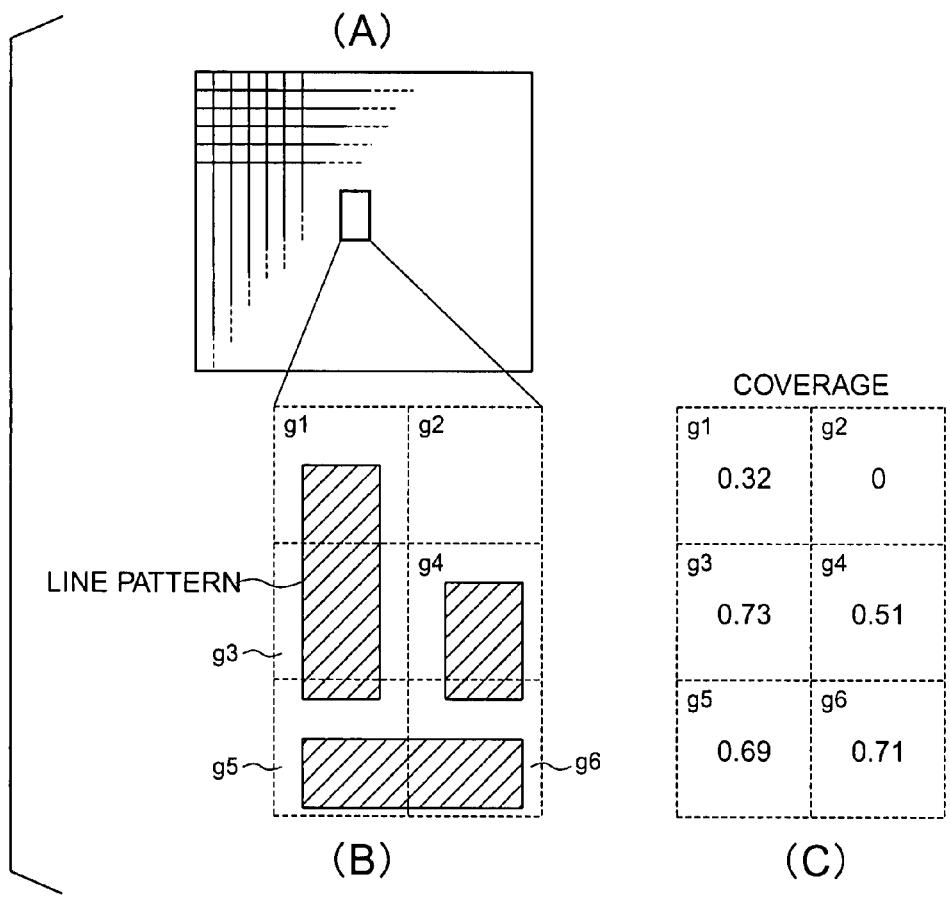
FIG. 3 is a diagram showing exemplary coverages calculation in the defect inspecting apparatus.

The coverage/edge density calculating section 3 uses design data (mask data) to calculate the coverage and edge density of each grid cell. The coverage is the line density (=area of line/area of grid cell) in the grid cell. For example if line occupies the entire area of a grid cell, the coverage of the cell is 1; if no line is in a grid cell, the coverage of the cell is 0. An example of coverage calculation is shown in FIG. 3. FIG. 3A shows an inspection region divided into subregions in a grid pattern. FIG. 3B shows an enlarged view of a portion of the inspection region. Line patterns are formed in grid cells g1 to g6 as shown in FIG. 3B. The coverages of the gird cells g1 to g6 are shown in FIG. 3C. Since no line pattern is formed in grid cell g2, the coverage of the grid cell is 0.

Figure 4:
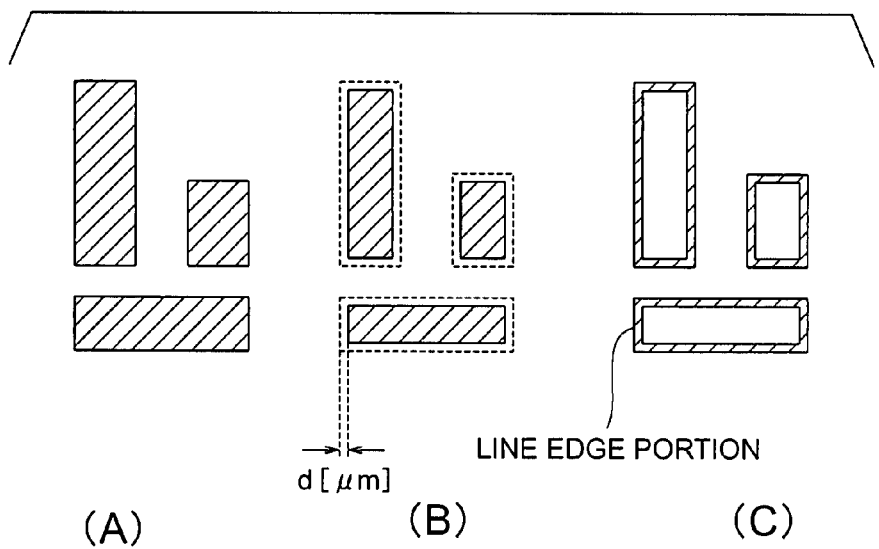
FIG. 4 is a diagram illustrating exemplary edge density calculation in the defect inspecting apparatus.
Figure 5:
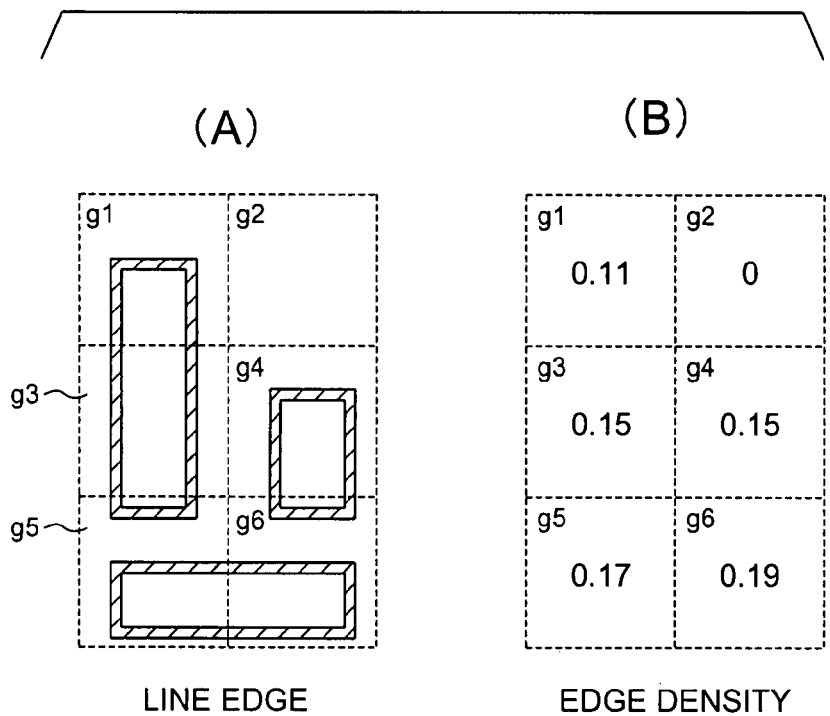
FIG. 5 is a diagram illustrating exemplary edge density calculation in the defect inspecting apparatus.
Figure 6:
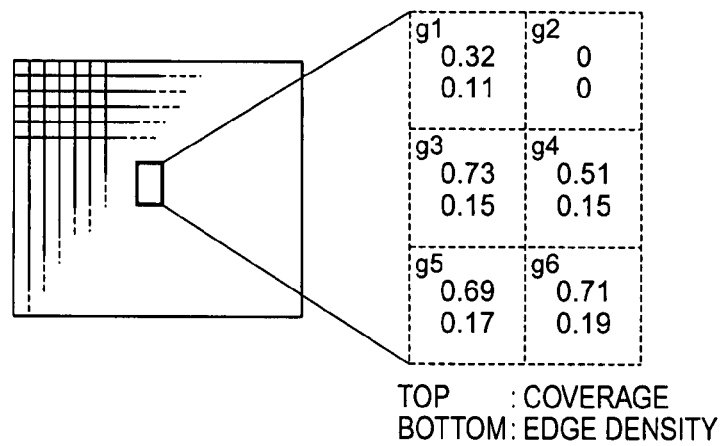
FIG. 6 is a diagram illustrating exemplary edge density calculation in the defect inspecting apparatus.

An example of calculation of the edge density of each grid cell g1 to g6 is shown in FIGS. 4 and 5. The edge density is the density of the edges of wiring lines (boundaries between wiring lines and the base surface). A method for calculating the edge density will be described. First, a line pattern (FIG. 4A) in a region whose edge density is to be calculated is reduced in both vertical and horizontal directions by d [μm] (FIG. 4B). Here, "d" is chosen to be a sufficiently small value relative to the line width. The original pattern region minus the reduced pattern region (FIG. 4C) is the edge portion of the pattern. The line edge portions in grid cells g1 to g6 are as shown in FIG. 5A. The edge densities (=area of edge portion/area of grid cell) of the grid cells are shown in FIG. 5B. Exemplary coverages and edge densities of grid cells g1 to g6 obtained are shown in FIG. 6.

Figure 7:
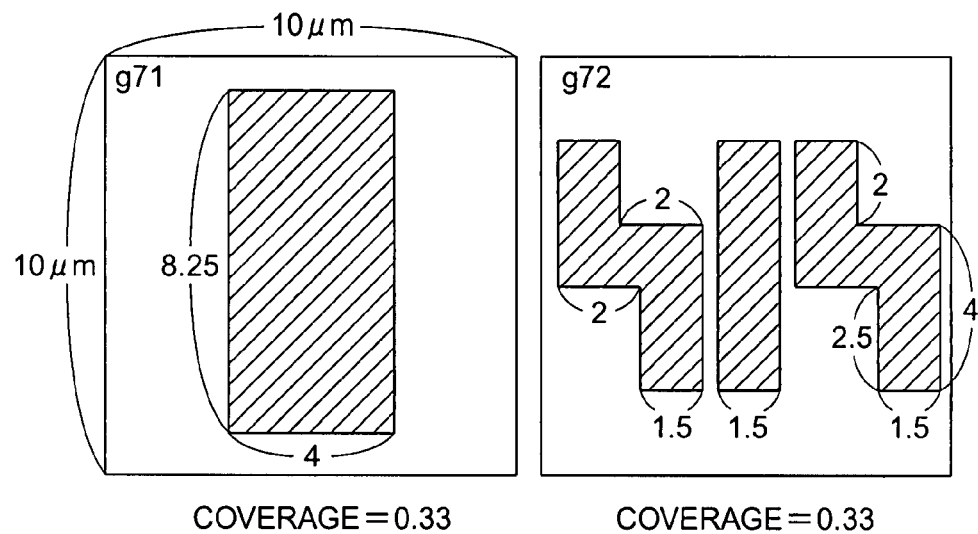
FIG. 7 is a diagram illustrating exemplary edge density calculation in the defect inspecting apparatus.
Figure 8:
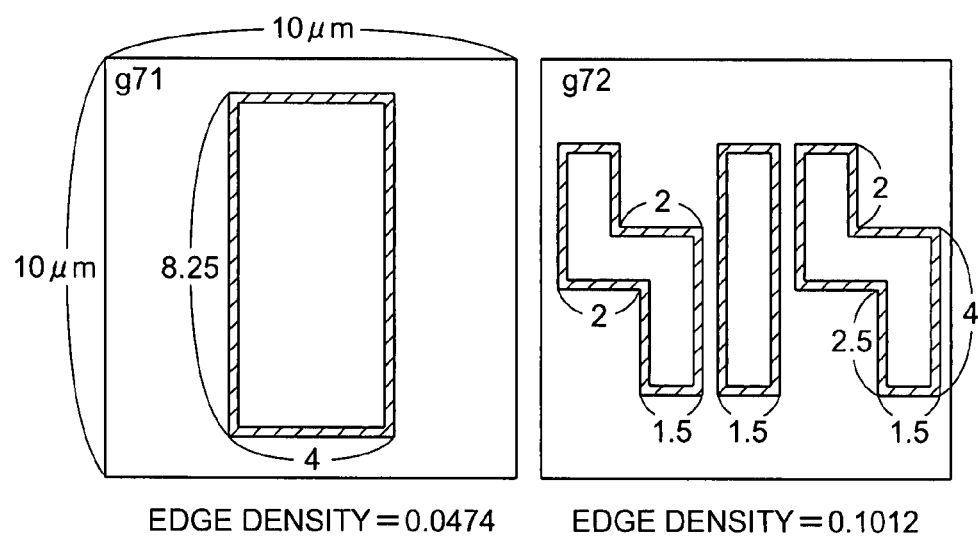
FIG. 8 is a diagram illustrating exemplary edge density calculation in the defect inspecting apparatus.

FIGS. 7 and 8 show another example of calculation of edge densities. As shown in FIG. 7, line patterns are formed with a coverage of 0.33 in square grid cells g71 and g72, 10 [μm] on a side. While the coverages are the same, grid cell g72 has a more complex line pattern formed in it. The patterns formed in grid cells g71 and g72 are reduced in vertical and horizontal directions by 0.2 (=d) [μm] and the reduced patterns are subtracted from the original patterns to obtain edge portions as shown in FIG. 8. The edge density of grid cell g71 will be 0.0474 and the edge density of grid cell g72 will be 0.1012. In this way, the edge density of each grid cell can represent the complexity of a line pattern in the grid cell. Because the intensity of reflected inspection light in a defect inspection is affected by the pitch of line and space in addition to the coverage, the edge density is calculated and used for setting sensitivity ranks in the embodiment.

Figure 9:
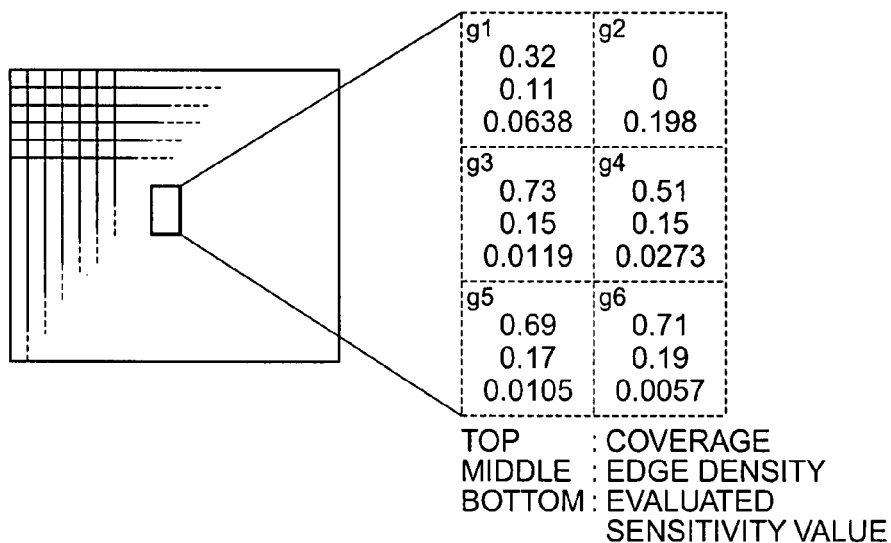
FIG. 9 is a diagram illustrating exemplary evaluated sensitivity value calculation in the defect inspecting apparatus.

The sensitivity rank setting section 4 calculates an evaluated sensitivity value (pattern density) from the coverage and edge density of each grid cell and assigns a sensitivity rank to the grid cell on the basis of the evaluated sensitivity value. The evaluated sensitivity value "ev" can be obtained using the following equation.

$$\text{Evaluated sensitivity value } ev(i)=(\text{maximum coverage}-\text{coverage}(i))*(\text{maximum edge density}-\text{edge density}(i))$$

where "maximum coverage" is the highest of the coverages of all grid cells, "maximum edge density" is the highest of edge densities of all grid cells, and "i" is a grid cell number. FIG. 9 shows an example of evaluated sensitivity values calculated for grid cells g1 to g6. The highest coverage of all grid cells, including grid cells g1 to g6, is 0.9 and the highest edge density is 0.22.

Figure 10:
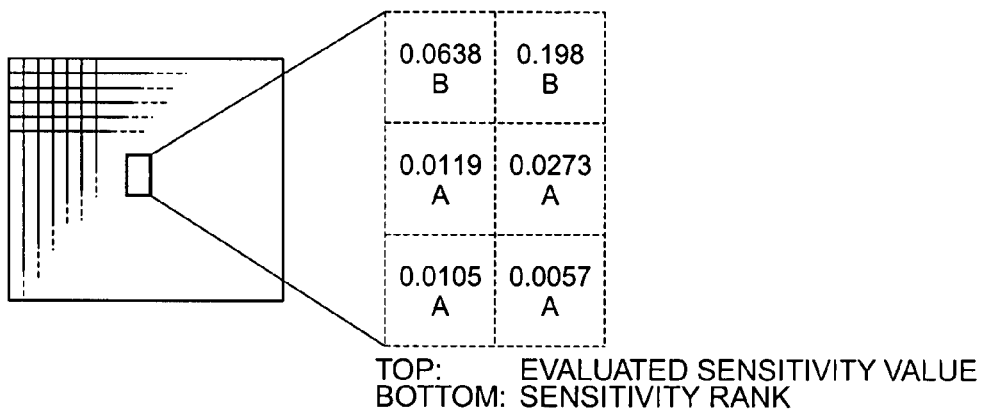
FIG. 10 is a diagram showing exemplary sensitivity rank assignment in the defect inspecting apparatus.

Based on the evaluated sensitivity values thus calculated, sensitivity ranks are assigned to the grid cells. Here, the grid cells are classified into two ranks, low and high. The median or average value of the evaluated sensitivity values is set as the boundary value and grid cells having evaluated sensitivity values greater than or equal to the boundary value are assigned the low sensitivity rank and grid cells having evaluated sensitivity values less than the boundary value is assigned the high sensitivity rank. FIG. 10 shows exemplary sensitivity ranks assigned. The boundary value is set to 0.05. Rank A is the low sensitivity rank and rank B is the high sensitivity rank.

The inspection execution region setting section 5 groups grid cells having the same sensitivity rank together and divides the resulting polygon into rectangles to set inspection execution regions. This is done because the defect inspecting apparatus performs a defect inspection on a rectangular inspection region.

The process for dividing the polygon of grouped grid cells into rectangles includes the step of reducing the number of vertices of the polygon to simplify the shape and the step of dividing the simplified polygon into rectangles.

Figure 11:
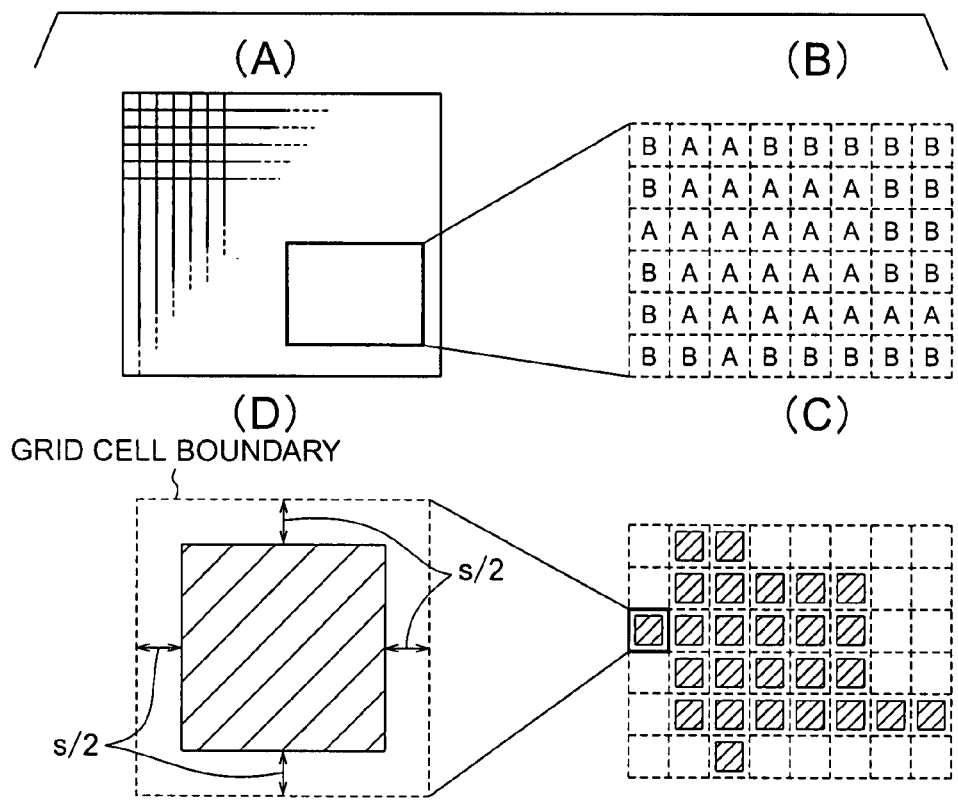
FIG. 11 is a diagram showing an exemplary simplifying process in the defect inspecting apparatus.
Figure 12:
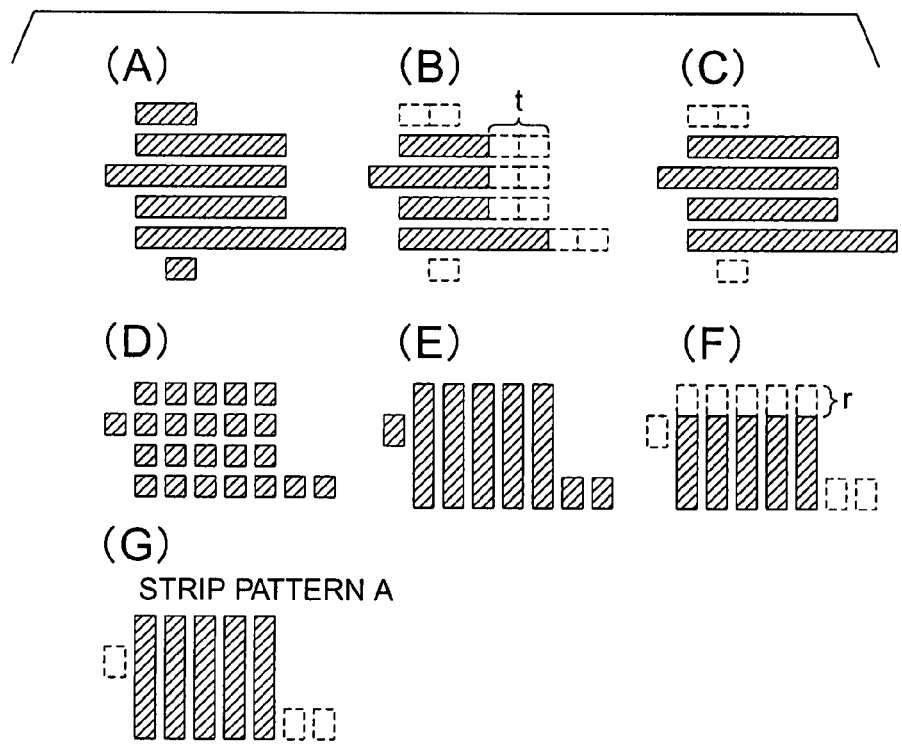
FIG. 12 is a diagram showing the exemplary simplifying process in the defect inspecting apparatus.
Figure 13:
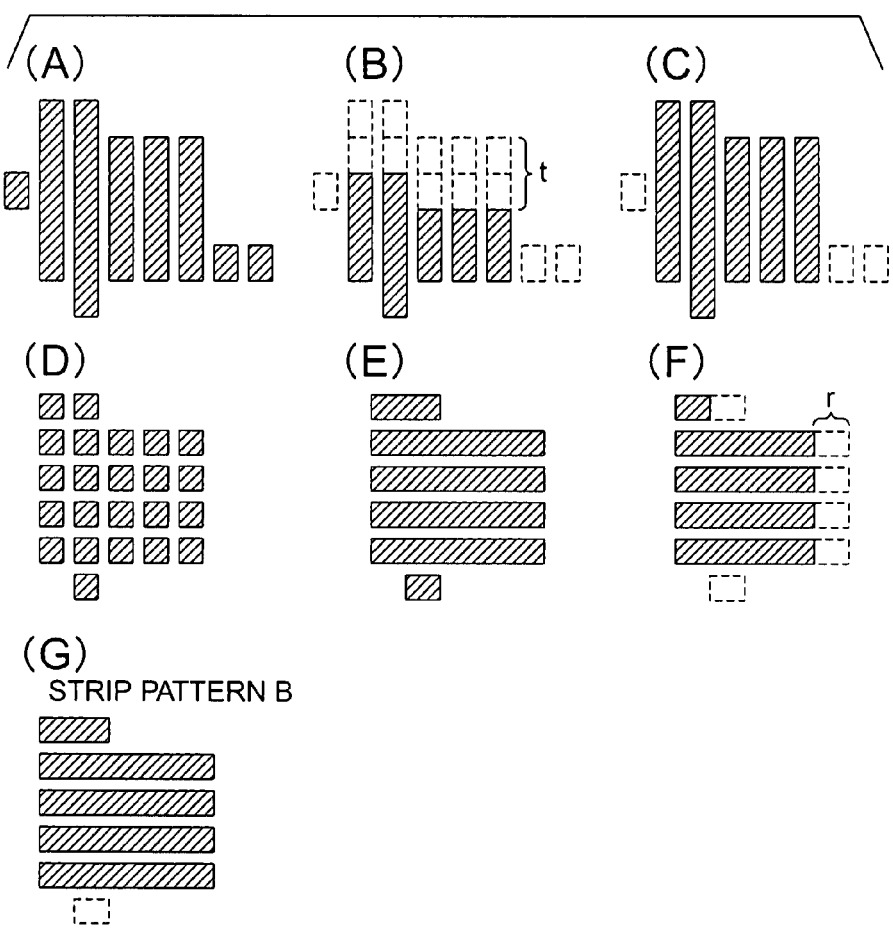
FIG. 13 a diagram showing the exemplary simplifying process in the defect inspecting apparatus.

The step of reducing the number of vertices of the grouped polygon to simplify the polygon will be described first with reference to FIGS. 11 to 15. FIG. 11A shows an inspection region divided into grid cells and FIG. 11B shows an enlarged view of a portion of the inspection region. Each grid cell has been assigned a sensitivity rank. The process starts with regions assigned the low sensitivity rank (rank A).

First, rectangles are generated in each grid cell that is assigned the rank of interest (rank A) as shown in FIG. 11C. The rectangle generated is smaller than a grid cell by s/2 in four directions as shown in FIG. 11D. That is, the rectangle generated is smaller than the grid cell by "s" in both vertical and horizontal directions. Here, "s" is any value smaller than one side of the grid cell.

Then, each of the generated rectangles is enlarged by "s" in the horizontal directions. As a result, the rectangles are connected together in the horizontal directions into strip shapes as shown in FIG. 12A.

Then, each strip is reduced by a length "t" in the horizontal direction. This process eliminates strips having lengths less than or equal to "t" as shown in FIG. 12B. The greater the value of "t", the more vertices of the polygon are removed.

Then, each of the strips is enlarged in the horizontal direction by "t" as shown in FIG. 12C. Strips eliminated by the previous operation remain eliminated.

This pattern (FIG. 12C) is ANDed with the original rectangular pattern (FIG. 1C) to obtain a rectangular pattern as shown in FIG. 12D.

Then, each rectangle is enlarged by a length "s" in the vertical directions. As a result, the rectangles are connected together in the vertical direction into strip shapes as shown in FIG. 12E.

Then, each strip is reduced by a length "r" in the vertical direction. This reduction eliminates strips having a length less than or equal to "r" as shown in FIG. 12F. The greater the value of "r", the more vertices of the polygon are removed. Here, s, r, and t are preferably such that s<r<t.

Then, each strip is enlarged in the vertical direction by a length "r" to obtain a strip pattern A as shown in FIG. 12G. The strips eliminated in the previous operation remain eliminated.

Then, the process described above is repeated but now the operation in the horizontal direction and the operation in the vertical directions are replaced with each other.

First, each of the rectangles shown in FIG. 11C is enlarged by a length "s" in the vertical directions. As a result, the rectangles are connected together in the vertical directions into strip shapes as shown in FIG. 13A.

Then, each strip is reduced by a length "t" in the vertical direction. This reduction eliminates strips having lengths less than or equal to "t" in the vertical direction as shown in FIG. 13B.

Each strip is then enlarged by "t" in the vertical direction as shown in FIG. 13C. The strips eliminated by the previous operation remain eliminated.

This pattern (FIG. 13C) is ANDed with the original pattern (FIG. 11C) to obtain a rectangular pattern as shown in FIG. 13D.

Then, each of the rectangles is enlarged by a length "s" in the horizontal directions. As a result, the rectangles are connected together in the horizontal direction into strip shapes as shown in FIG. 13E.

Each strip is then reduced by a length "r" in the horizontal direction. This reduction eliminates strips having lengths less than or equal to "r" in the horizontal direction as shown in FIG. 13F.

Then, each strip is enlarged by "r" in the horizontal direction to obtain a strip pattern B as shown in FIG. 13G. The strips eliminated by the previous operation remain eliminated.

Figure 14:
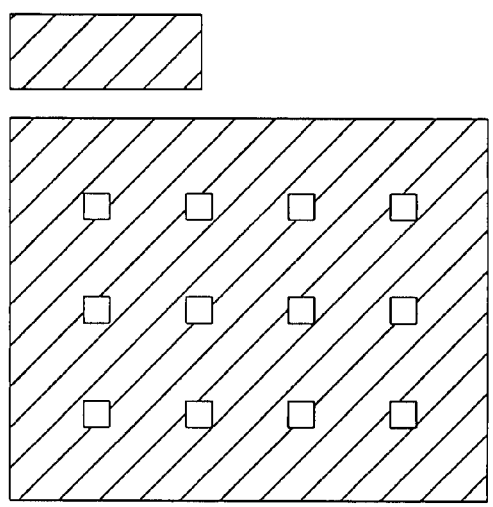
FIG. 14 a diagram showing the exemplary simplifying process in the defect inspecting apparatus.

Strip patterns A and B obtained as a result of the processes described above are ORed with each other. The sole use of strip pattern A would eliminate regions that have lengths less than or equal to "t" in the horizontal direction but are long in the vertical direction; the sole use of strip pattern B would eliminate regions that have a length less than or equal to "t" in the vertical direction but are long in the horizontal direction. Therefore two strip patterns are ORed with each other to provide a combined pattern as shown in FIG. 14, thereby avoiding elimination of regions that are short in the vertical or horizontal direction but long in the other direction.

Figure 15:
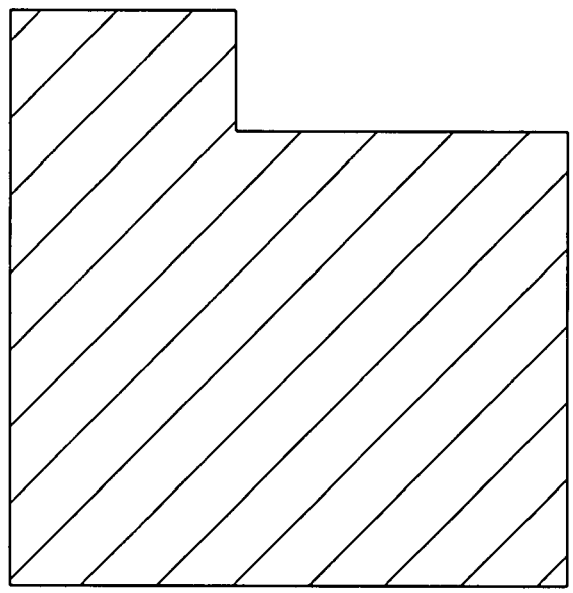
FIG. 15 a diagram showing the exemplary simplifying process in the defect inspecting apparatus.

The combined pattern is enlarged on a grid cell basis by a length of s/2 in four directions to provide a polygon having a reduced number of vertices as shown in FIG. 15.

As a result of the simplifying step as described above, the regions with rank A shown in FIG. 11B is transformed to a simplified polygon region having fewer vertices as shown in FIG. 15.

Figure 16:
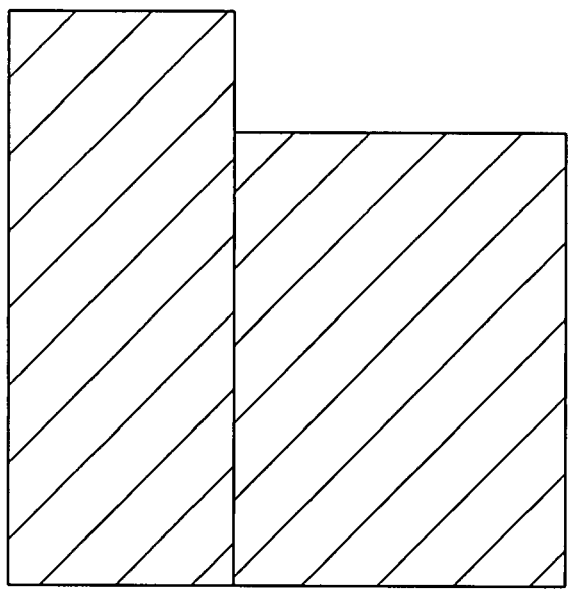
FIG. 16 a diagram showing an exemplary process for dividing a region into rectangles in the defect inspecting apparatus.
Figure 17:
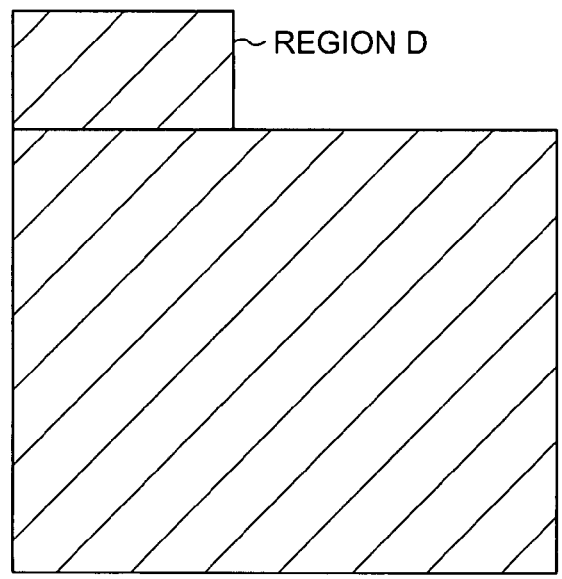
FIG. 17 is a diagram showing another exemplary process for dividing a region into rectangles in the defect inspecting apparatus.

Then, at the step of dividing the simplified polygon into rectangles, the polygon obtained at the simplifying step is divided into rectangles as shown in FIG. 16. While the polygon is divided in the vertical direction in this example, the polygon may be divided in the horizontal direction as shown in FIG. 17. One of the rectangles produced at the step of dividing into rectangles that has a smaller area, like region D in FIG. 17, may be excluded from an inspection on rank A regions. The excluded region is included in a group of rank-B inspection region.

Figure 18:
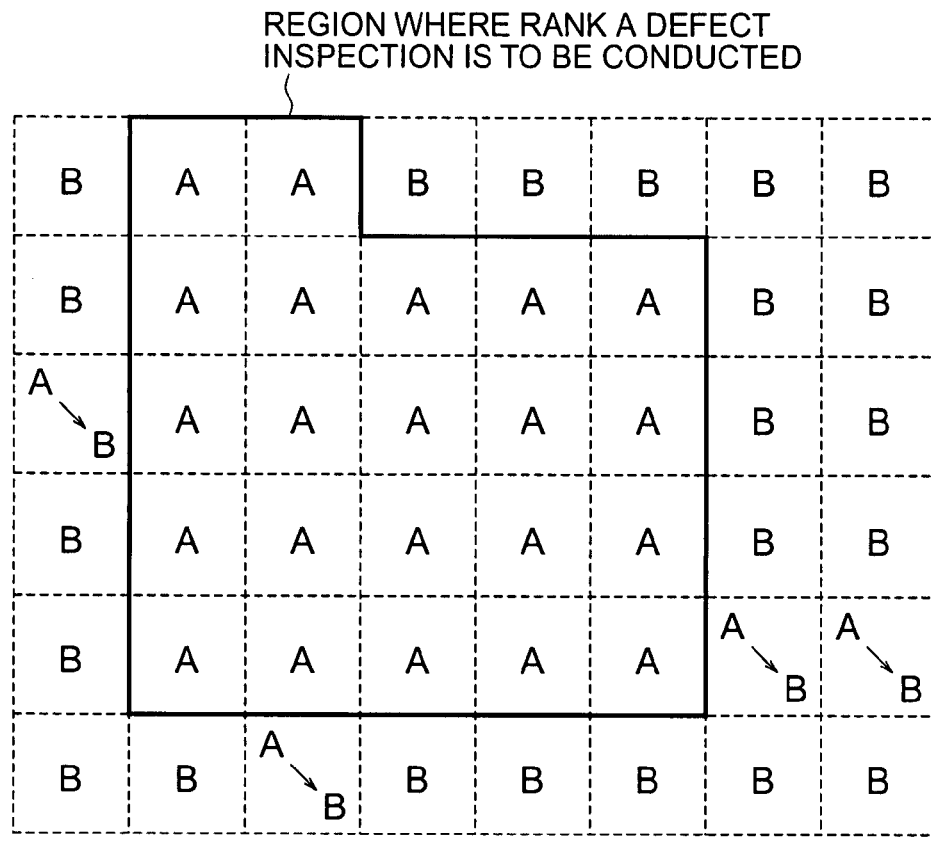
FIG. 18 is a diagram showing exemplary sensitivity rank reassignment in the defect inspecting apparatus.

As shown in FIG. 18, grid cells that are excluded from the rank A inspection region as a result of the simplifying step are assigned the high sensitivity rank (rank B). The rank-B region is a high-sensitivity region where defects can be easily detected. If a defect inspection intended for low-sensitivity regions where defects are hard to be detected were conducted on this region, it would become more likely to false defects to be generated. The simplifying process is started with the low-sensitivity (rank A) regions in the embodiment in order to prevent generation of false defects.

Figure 19:
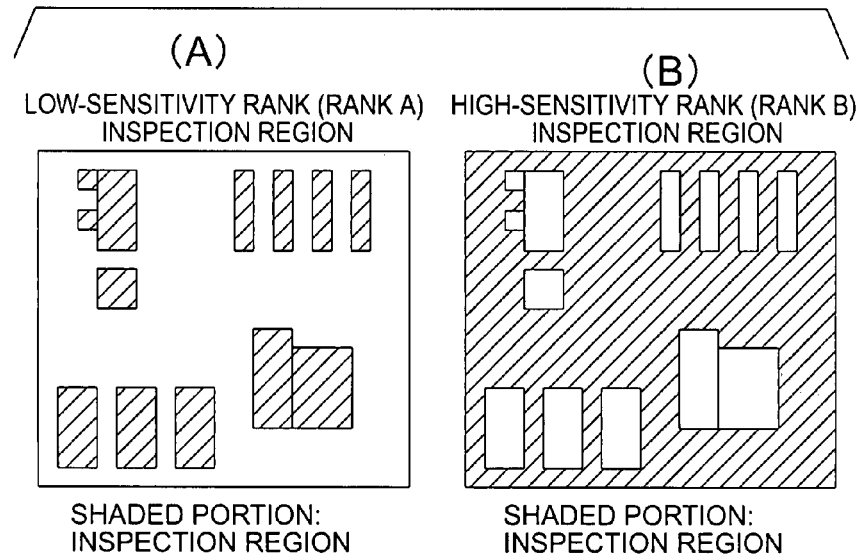
FIG. 19 is a diagram showing an exemplary defect inspection execution region in the defect inspecting apparatus.

The region excluding rank A regions obtained as a result of the process described above are the rank-B regions. For example, if rank A inspection regions as shown in FIG. 19A is obtained, the rank-B regions will be as shown in FIG. 19B.

Information about inspection regions with the sensitivity ranks assigned by the inspection execution region setting section 5 is sent to the defect inspecting section 6. A defect inspection is conducted on an actual wafer in the defect inspection section 6, defects are classified by the defect classifying section 7, and the false defect rate is measured. The defect inspection involves generation of images with an image sensor (not shown) and comparison of the generated images with reference images. The reference images are an image of a wafer (chips) inspected in the last inspection and an image of a wafer (chips) inspected in the last but one inspection. Images are compared with the two reference images to detect defects.

Setting of inspection parameters such as the light level and the received light intensity threshold, the defect inspection, and the classification of defects are repeated until the false defect rate decreases to a predetermined level or lower. In this way, appropriate inspection parameters are set for each sensitivity rank. In addition to the information about inspection regions having each sensitivity rank, the coordinate system of mask data is sent to the defect inspecting section 6 and is converted into the coordinate system of the defect inspecting section 6.

The set inspection parameters and typical evaluated sensitivity value in the inspection region are stored in the sensitivity library 8. The typical evaluated sensitivity value is used to search the sensitivity library 8 to retrieve the inspection parameters in the subsequent defect inspections. Thus, setting of inspection parameters can be automated and the time required for setting inspection parameters can be reduced.

Defects detected by a defect inspection are stored in the defect data memory 9. Also, a wafer map or a chart is displayed on the display 10 so that a user can check to see whether there are defects.

In this way, the defect inspecting apparatus according to the first embodiment of the present invention enables appropriate sensitivity ranks to be assigned to inspection regions. Furthermore, the shapes and the number of inspection region can be within the tolerance level of the defect inspecting apparatus.

SECOND EMBODIMENT

Figure 20:
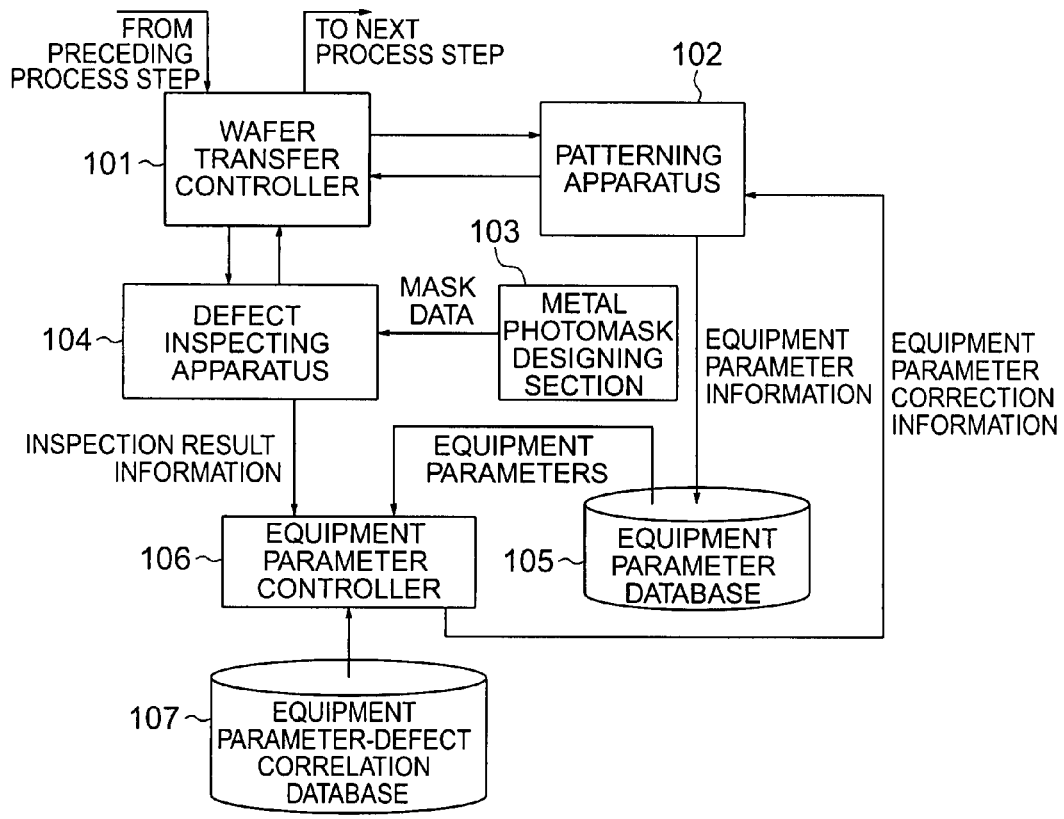
FIG. 20 is a diagram schematically showing a configuration of a semiconductor manufacturing system according to a second embodiment of the present invention.

FIG. 20 schematically shows a configuration of a semiconductor manufacturing system according to a second embodiment of the present invention. The defect inspecting apparatus 104 is the defect inspecting apparatus according to the first embodiment. A wafer that underwent the preceding process steps (such as wafer cleaning and formation of thin-films and MOS transistors) is transferred by a wafer transfer controller 101 to a patterning apparatus 102. In the patterning apparatus 102, first a wiring metal film is formed by sputtering or CVD (chemical vapor deposition). Then, a resist (positive resist in which the portion that is exposed to light becomes soluble) is applied and a wiring pattern is transferred to the wafer through a metal photomask by exposure to light. The portion of the resist that is illuminated with light is solved with a developer to form a resist mask. The wiring metal film is etched using the resist mask and the resist is removed to form a line pattern.

Equipment parameter information (such as a light exposure, a focus value, and the temperature of the developer) of the patterning apparatus 102 during formation of the line pattern is monitored with a sensor (not shown) attached to the patterning apparatus 102 and is sent to an equipment parameter database 105.

The patterned wafer is transferred by the wafer transfer controller 101 to the defect inspecting apparatus 104. Mask data is input in the defect inspecting apparatus 104 from a metal photomask designing section 103. Based on the mask data, an inspection region is divided, the coverages and edge densities are calculated, a sensitivity rank is assigned to each subregion, inspection execution regions are set, and then a defect inspection is performed.

Inspection result information is input in an equipment parameter controller 106 from the defect inspecting apparatus 104. Equipment parameters used in pattern formation on the wafer inspected are input from the equipment parameter database 105. An equipment-parameter-defect correlation database 107 contains information about the correlation between defects that occurred and equipment parameters. When a defect is detected by a defect inspection, the equipment parameter controller 106 searches the equipment-parameter-defect correlation database 107 for information about the correlation between the defect and equipment parameters, determines an equipment parameter that should be controlled and its correction value from the correlation information and the equipment parameters, and outputs equipment parameter correction information to the patterning apparatus 102. The patterning apparatus 102 corrects the equipment parameter in accordance with the equipment parameter correction information.

Because an appropriate sensitivity rank is set on the basis of the coverage and edge density in the defect inspecting apparatus 104, defects can be accurately detected. Furthermore, since the shape of an inspection execution region is simplified and divided into rectangles, the time required for a defect inspection can be reduced.

Because defects that correlated with an equipment parameter is accurately detected and the equipment parameter is corrected in an early stage, the same type of defect can be prevented from occurring on wafers to be processed in the next and subsequent manufacturing processes and yields of semiconductor device manufacturing can be increased. If the semiconductor devices manufactured have a multilayer structure, defects can be quickly detected by performing a defect inspection each time a line pattern of a layer has been formed, and the result of the inspection can be quickly reflected in equipment parameters.

In addition to correction of equipment parameters, cleaning of equipment, modification to the manufacturing process and the apparatus, change of the apparatus may be made on the basis of the result of an inspection by the defect inspecting apparatus 104. Modifications to the manufacturing process may include addition of a cleaning process, for example, to circuit pattern formation which involves multiple processes. Thus, the cause of defects that cannot be solved by correction of equipment parameters alone can be solved.

Thus, the semiconductor manufacturing system according to the second embodiment of the present invention is capable of setting an appropriate sensitivity rank for each appropriate inspection region and performing a defect inspection, thereby preventing defects on the basis of the result of the inspection and improving manufacturing yields.

The sensitivity rank setting section 4 may set three or more sensitivity ranks instead of the two sensitivity ranks, low and high. In case of setting three sensitivity ranks, the inspection execution region setting section 5 performs the simplifying process and the dividing process, starting with the regions with the lowest sensitivity rank. The chip region excluding the regions with the lowest sensitivity and the region with the second lowest sensitivity is inspected as the inspection execution region assigned the highest sensitivity. However, it must be taken into consideration that a longer time is required for creating a recipe of the defect inspecting apparatus because the defect inspecting section 6 sets inspection parameters for every rank. The coverage/edge density calculating section 3 may calculate the circumference of the line pattern in each inspection subregion, instead of the density of the edge portion of line. The circumference of the line pattern can represent the pitch of line and space.

While coverages and edge densities are used by the sensitivity rank setting section 4 to calculate evaluated sensitivity values and set sensitivity ranks for grid cells in the embodiments described above, only edge densities may be used to set the sensitivity ranks for the grid cells. If the two sensitivity ranks, low and high, are used, grid cells having edge densities higher than or equal to a boundary value are assigned the low sensitivity rank (rank A) and grid cells having edge densities lower than the boundary value are assigned the high sensitivity rank (rank B). The boundary value may be the median or average value of edge densities.

Figure 21:
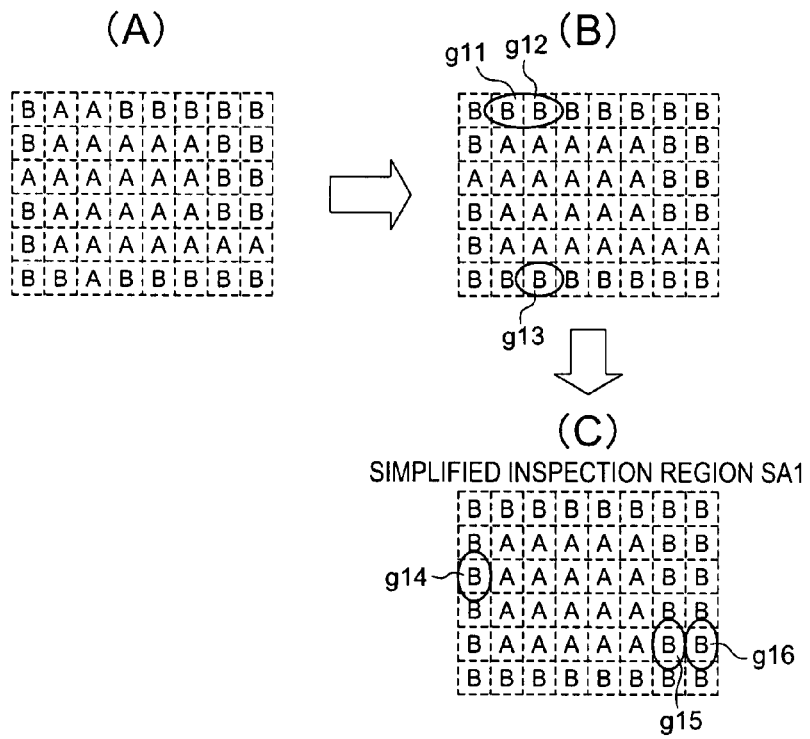
FIG. 21 is a diagram showing another exemplary simplifying process in the defect inspecting apparatus.

The inspection execution region setting section 5 may set inspection execution regions as follows. It is assumed here that sensitivity ranks have been assigned to inspection subregions in a grid shape as shown in FIG. 21A.

First, the inspection subregions having the low sensitivity rank (rank A) in each row is counted and, if the number of the inspection subregions having rank A is less than or equal to "m" (where "m" is 2), the inspection subregions having rank A in the row are reassigned rank B. Grid cells g11, g12, and 13 are reassigned rank B as shown in FIG. 21B. Then, the inspection subregions having rank A in each column are counted and, if the number of the inspection subregions having rank A is less than or equal to "n" (where n is 1), the inspection subregions having rank A in the column are reassigned rank B. Grid cells g14, g95, and g16 are reassigned rank B as shown in FIG. 21C. Thus, simplified inspection region SA1 is obtained.

Figure 22:
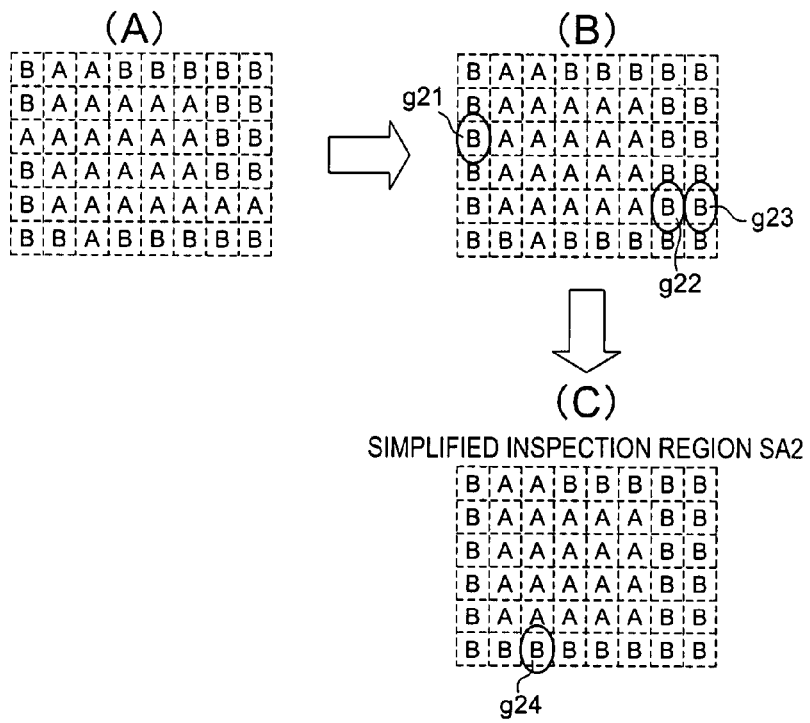
FIG. 22 is a diagram showing yet another exemplary simplifying process in the defect inspecting apparatus.

Then, the inspection subregions having rank A in each column of inspection subregions shown in FIG. 22A (which is the same as FIG. 21A) are counted and, if the number of the inspection subregions having rank A in the column is less than or equal to "m" (where m=2), the inspection subregions having rank A in the row are reassigned rank B. As shown in FIG. 22B, grid cells g21, g22, and g23 are reassigned rank B. Then, the inspection subregions having rank A in each row are counted and, if the number of the inspection subregions having rank A is less than or equal to "n" (where n=1), the inspection subregions having rank A are reassigned rank B. As shown in FIG. 22C, grid cell g24 is reassigned rank B. Thus, simplified inspection region SA2 is obtained.

Figure 23:
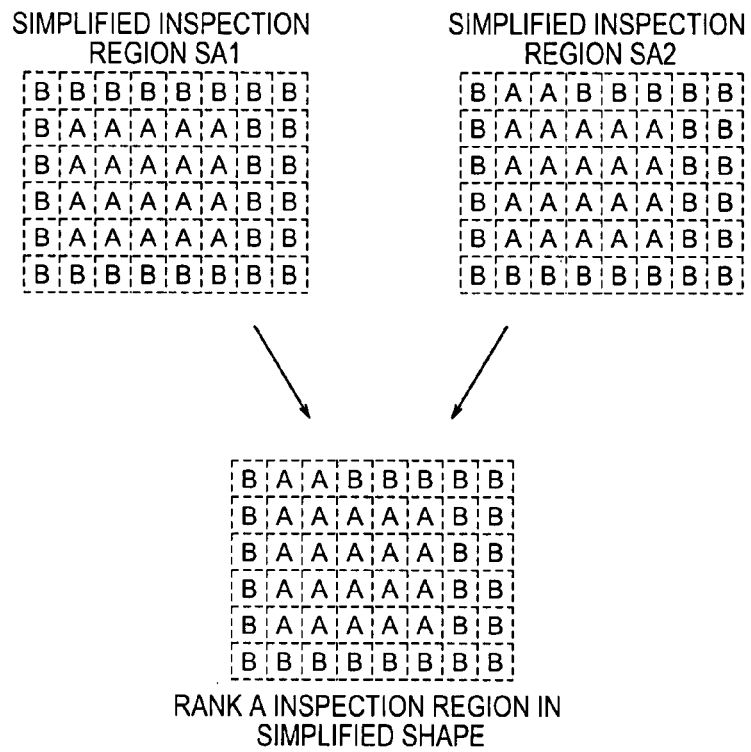
FIG. 23 is a diagram showing yet another exemplary simplifying process in the defect inspecting apparatus.
Figure 24:
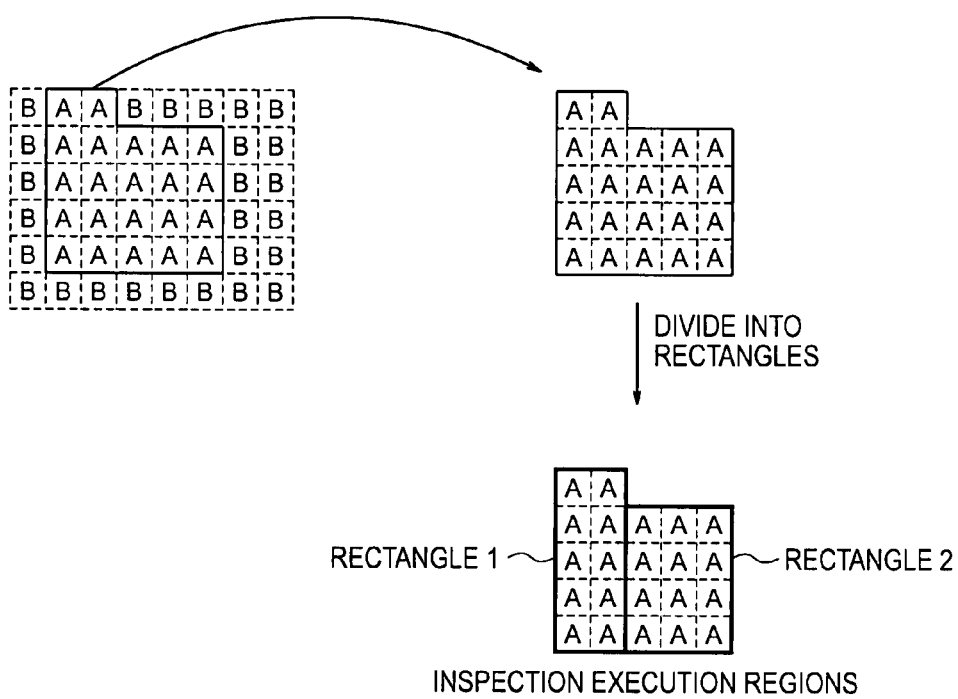
FIG. 24 is a diagram showing yet another exemplary simplifying process in the defect inspecting apparatus.

By reassigning rank A to inspection subregions assigned rank A in at least one of simplified inspection regions SA1 and SA2 and reassigning rank B to inspection subregions assigned rank B in both of inspection subregions SA1 and SA2, the shape of the rank A inspection region can be simplified as shown in FIG. 23. The rank A inspection region can be divided into rectangles (rectangles 1 and 2) as shown in FIG. 24 to set inspection execution regions.

In the foregoing, "m" and "n" can be set to any value in accordance with the number of grid cells. The greater the values of "m" and "n", the simpler the shape of the rank A inspection region will be. By choosing values n and m such that n<m, it can be prevented that a rank A inspection region in which the number of rank A subregions in one of the row or column directions is smaller and the number of rank A regions in the other direction is greater will be assigned rank B.

THIRD EMBODIMENT

Figure 25:
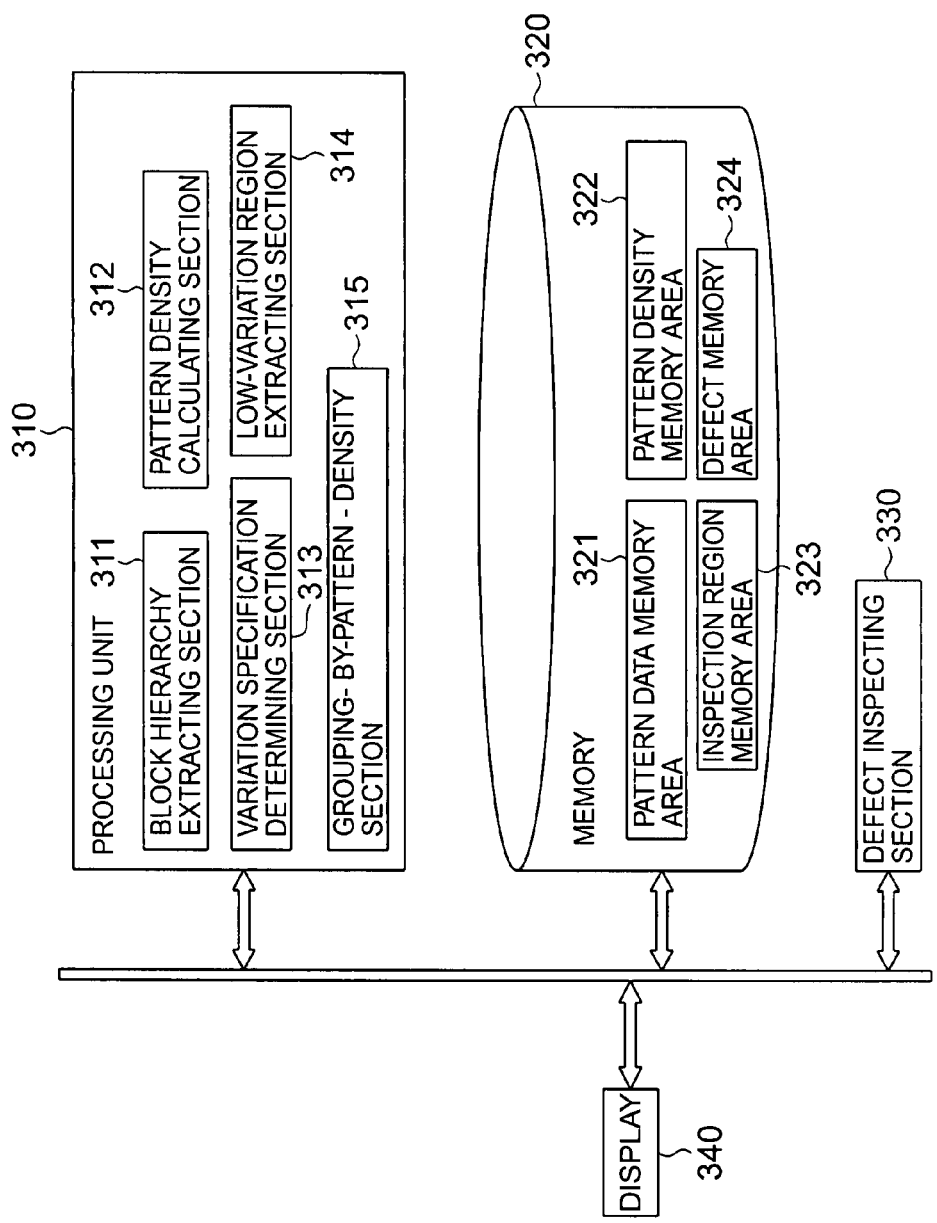
FIG. 25 is a diagram schematically showing a configuration of a defect inspecting apparatus according to a third embodiment of the present invention.

FIG. 25 schematically shows a configuration of a defect inspecting apparatus according to a third embodiment of the present invention. The defect inspecting apparatus according to the third embodiment includes a processing unit 310, a memory 320, a defect inspecting section 330, and a display 340.

The processing unit 310 includes a block hierarchy extracting section 311, a pattern density calculating section 312, a variation specification determining section 313, a low-variation region extracting section 314, and a grouping-by-pattern-density section 315.

The memory 320 includes a pattern data memory area 321, a pattern density memory area 322, an inspection region memory area 323, and a defect memory area 324.

The pattern data memory area 321 stores pattern data such as GDS. The pattern data includes the locations and sizes of blocks (IP). Each block consists of smaller blocks.

Figure 26:
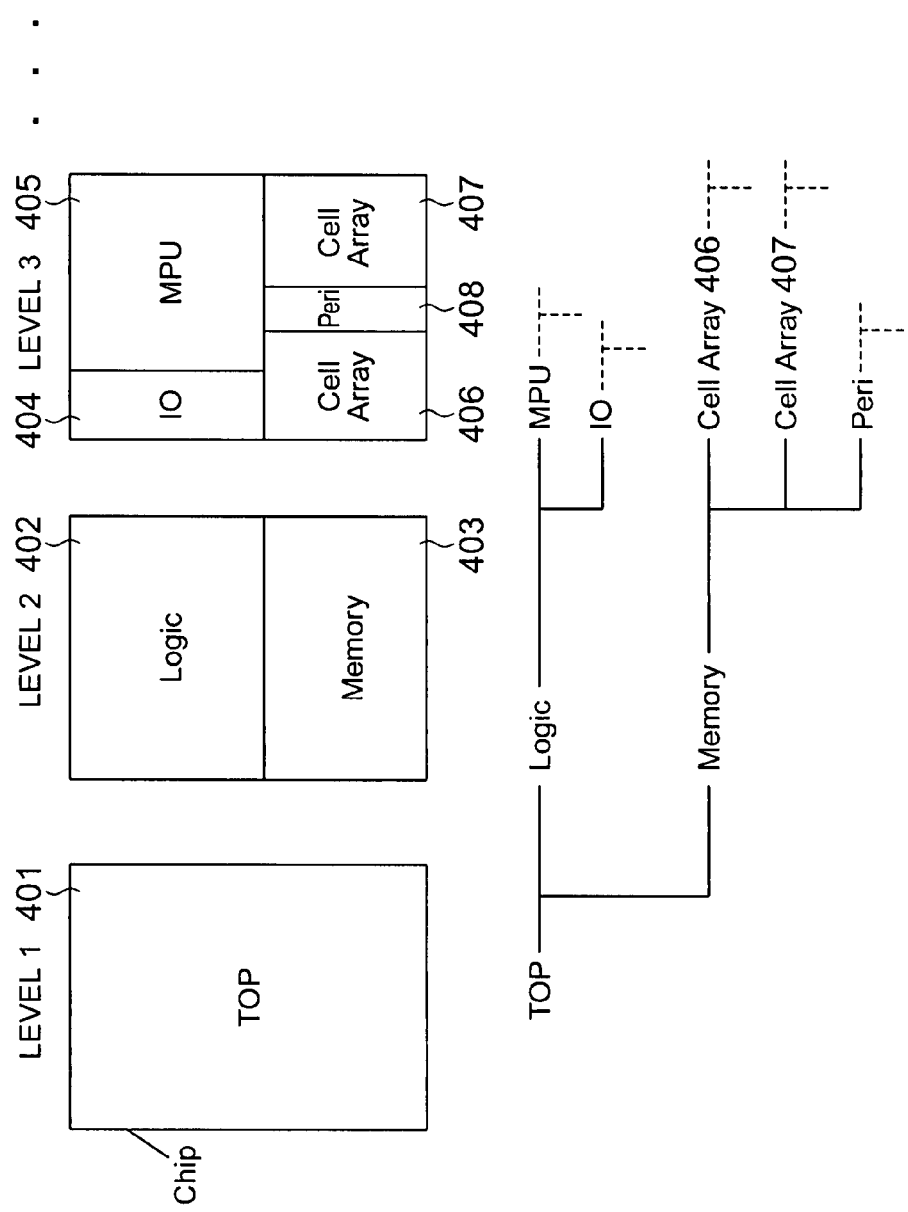
FIG. 26 is a diagram showing an exemplary hierarchical structure of pattern data.

The pattern data has a hierarchical structure, an example of which is shown in FIG. 26. At Level 1 is a top cell (TOP) 401. It can be seen from Level 2 that the top cell 401 consists of a logic 402 and a memory 403. It also can be seen from Level 3 that the logic 402 consists of an IO 404 and an MPU 405 and the memory 403 consists of cell arrays 406 and 407 and a peripheral circuit (Peri) 408. While the hierarchical structure only down to Level 3 is shown here, the blocks at Level 3 also consist of smaller blocks.

The block hierarchy extracting section 311 extracts hierarchy information as shown in FIG. 26 from the pattern data stored in the pattern memory area 321.

The pattern density calculating section 312 calculates the average pattern density and pattern density variation of each block at each level. The pattern density is any of the coverage, edge density, and evaluated sensitivity value. The coverage, edge density, and evaluated sensitivity value are calculated in the same way as in the first example and therefore description of which will be omitted.

The pattern density calculating section 312 divides each block into multiple regions (inspection subregions) and calculates the pattern density of each inspection subregion. The pattern density calculating section 312 then calculates the average value and variation of the pattern densities of each block. The variation may be the standard deviation, for example.

The pattern density calculating section 312 divides each block into inspection subregions in a grid shape, for example. Considering the stage precision of the apparatus, the size of each grid cell is preferably at least 10 μm on a side. The size of each grid cell is preferably 50 μm on a side at the maximum because a greater gird cell size can cause both low and high density patterns to be contained in a single grid cell.

Figure 27:
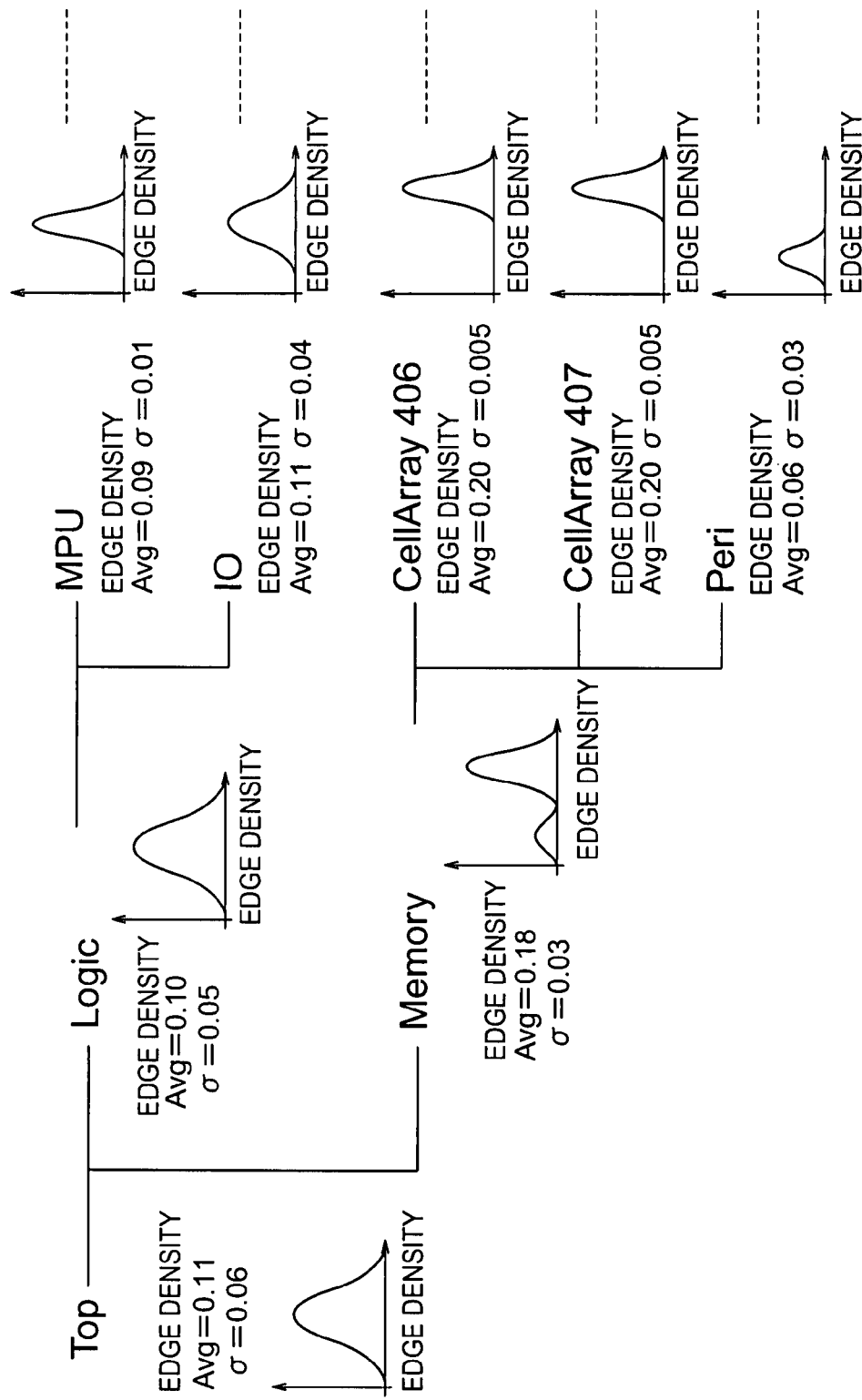
FIG. 27 is a diagram showing the average values and variations of edge densities of blocks.

FIG. 27 shows examples of calculated averages and variations of pattern densities of the blocks shown in FIG. 26. The pattern densities shown are edge densities. Blocks at higher levels include many patterns and therefore have greater pattern density variations whereas blocks at lower levels include fewer patterns and therefore have smaller pattern density variations.

The pattern density calculating section 312 stores the calculated average pattern densities and pattern density variations of the blocks in the pattern density memory area 322.

The defect inspecting apparatus classifies blocks into three groups: a group of blocks having small pattern density variations and large average pattern densities, a group of blocks having small pattern density variations and small average pattern densities, and a group having large pattern density variations. An inspection parameter (sensitivity) is set for each of the groups and a defect inspection is performed on the groups. An appropriate inspection parameter is set for the blocks belonging to the group having small pattern density variations so that the defect detection rate is improved.

The boundary value (threshold) of variation between the group having large pattern density variations and the group having small pattern density variations is herein referred to as a variation specification value. The variation specification value is determined by a variation specification determining section 313.

Figure 28:
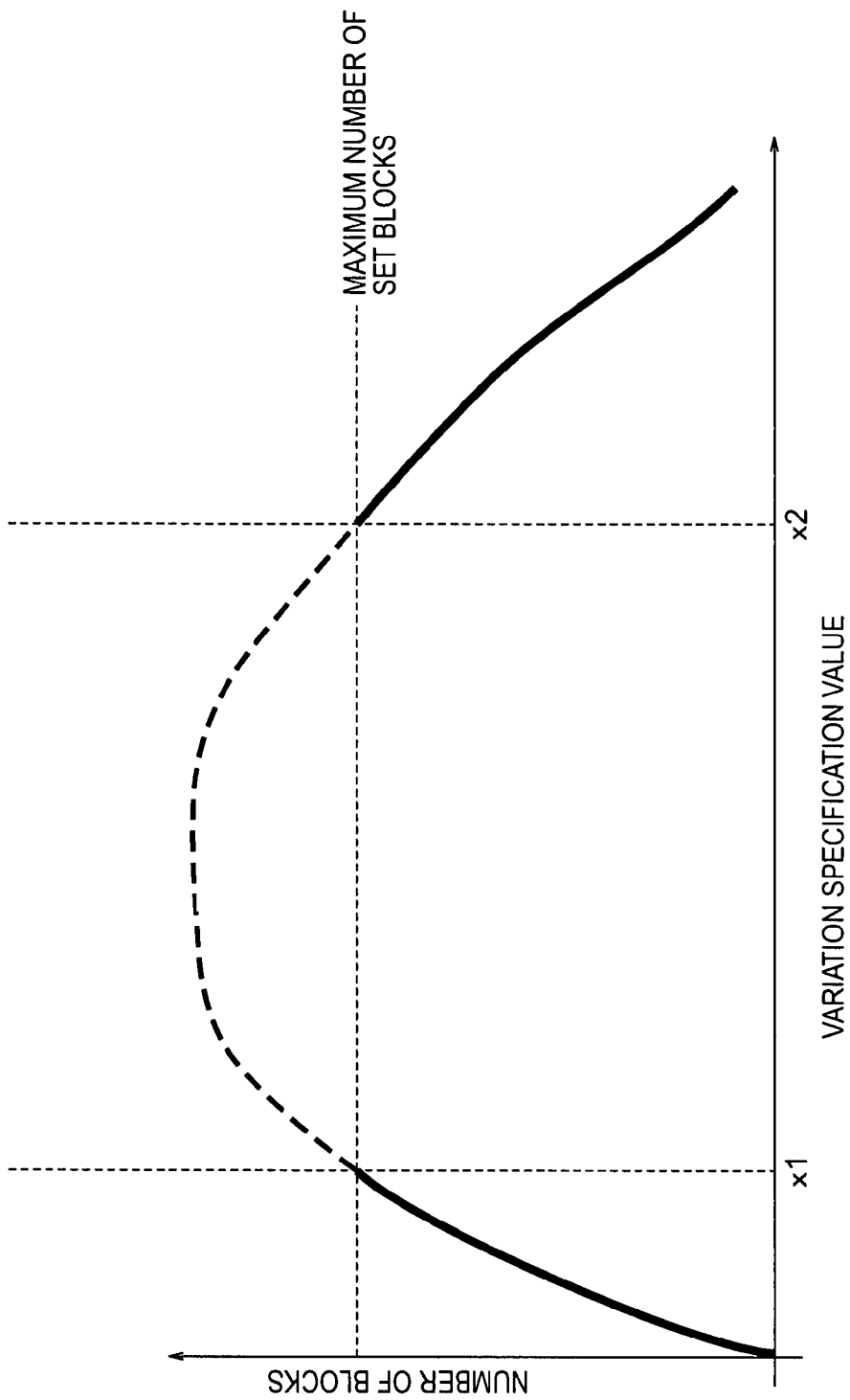
FIG. 28 is a graph of the relationship between a variation specification value and the number of blocks having pattern density variations less than the variation specification value.

FIG. 28 shows the relationship between the variation specification value and the number of blocks belonging to the group having small pattern density variations (less than the variation specification value).

The number of blocks having pattern density variations less than the variation specification value decreases as the variation specification value decreases. As the variation specification value increases, the number of blocks having pattern density variations less than the variation speck increases.

When the variation specification value increases up to a certain value, blocks at higher levels having many patterns and large variations are included in the group having small pattern density variations and therefore the number of blocks having pattern density variations less than the variation specification value decreases.

The graph shown in FIG. 28 can be obtained by changing the variation specification value from its initial value by a given increment and counting the blocks that belong to the group having small pattern density variations at each increment.

The number of blocks (regions) for which inspection parameters (sensitivities) can be set in the defect inspecting apparatus is predetermined and cannot be set to a value greater than the maximum number of set blocks (in the range from x1 to x2 shown). The variation specification value is set to a value less than or equal to x1 or greater than or equal to x2. The maximum number of set blocks varies from one apparatus to another and is typically in the range from several hundred to approximately one thousand.

Figure 29:
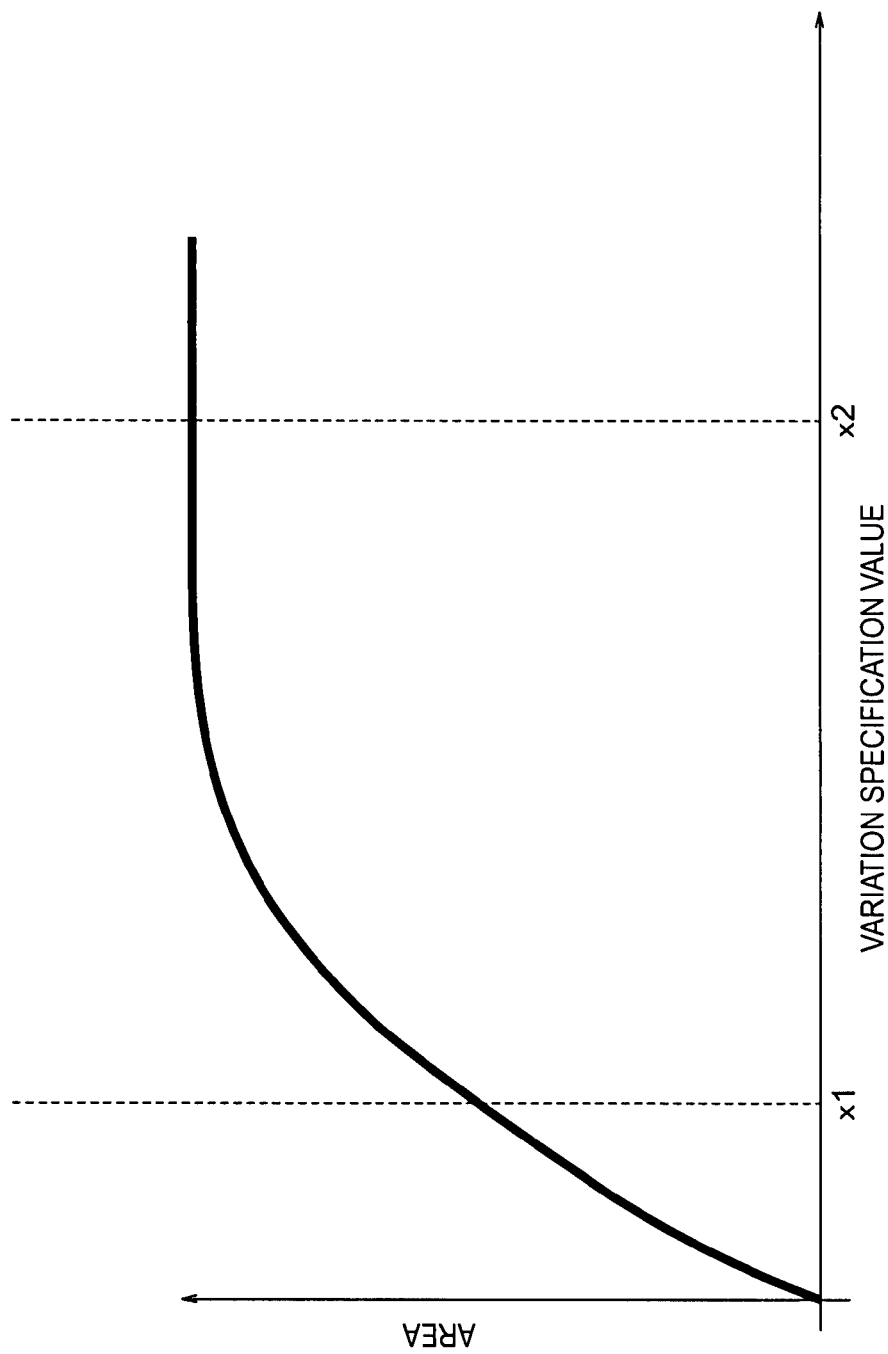
FIG. 29 is a graph of the relationship between the variation specification value and the total area of blocks having pattern density variations less than the variation specification value.

FIG. 29 shows the relationship between the variation specification value and the total area of blocks that belong to the group having small pattern density variations (less than the variation specification value).

The total area increases as the variation specification value increases.

When the variation specification value is less than or equal to x1, the pattern density variations are small and therefore the defect detection rate can be improved but the area that is inspected decreases. On the other hand, when the variation specification value is greater than or equal to x2, the area that is inspected can be increased but the pattern density variation increases and therefore the defect detection rate decreases. Whether the variation specification value should be set to a value less than or equal to x1 or greater than or equal to x2 depends on requirements of defect inspections to be conducted.

In this way, the variation specification determining section 313 determines a variation specification value. The determined variation specification value is stored in the pattern density memory area 322.

The low variation region extracting section 314 uses the determined variation specification value to extract blocks that belong to the group having small pattern variations (smaller then the variation specification value).

For example, if average values and variations of pattern densities shown in FIG. 27 have been obtained and the variation specification value (standard deviation $\pi$) is 0.02, MPU 405 and cell arrays 406 and 407 are extracted.

The grouping-by-pattern-density section 315 groups the extracted regions (blocks) into two groups: a group of blocks having high average pattern density values and a group of blocks having low average pattern density values. The boundary value (threshold) of the average pattern densities is predetermined in accordance with a pattern density parameter (coverage, edge density, or evaluated sensitivity value) used.

If the boundary value of average pattern density (edge density) values in the example shown in FIG. 27 is 0.1, cell arrays 406 and 407 are classified as members of the group having high average pattern density values and MPU 405 is classified as a member of the group having low average pattern densities. IO 404 and peripheral circuit (Peri) 408 that have not been extracted by the low-variation region extracting section 314 are classified as members of the group having large pattern density variations.

Figure 30:
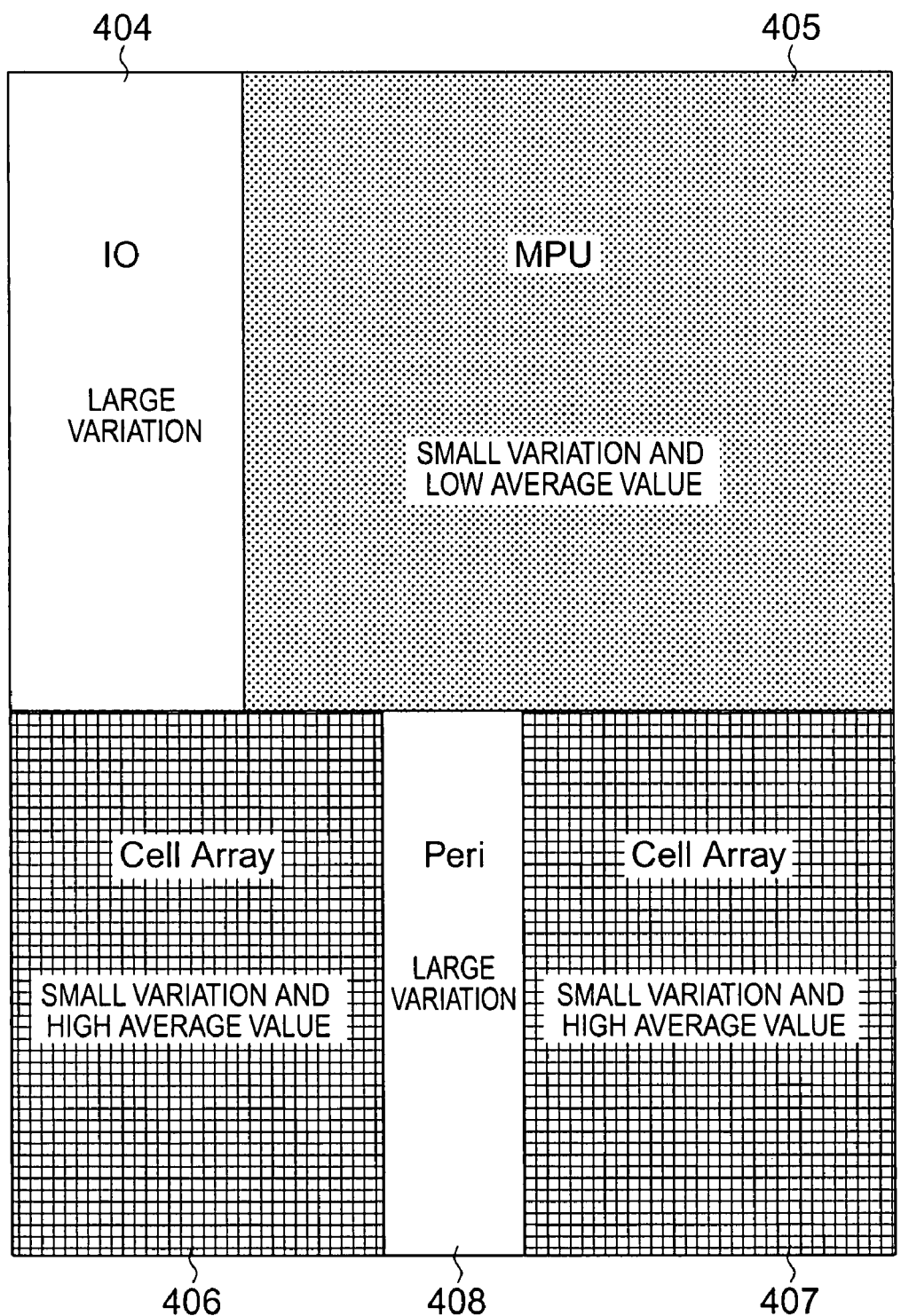
FIG. 30 is a diagram showing an example of grouping of blocks.

In this way, the blocks of the inspection region are grouped into three groups: the group of blocks having small pattern density variations and large average values, the group of blocks having small pattern density variations and small average values, and the group of blocks having large pattern densities, as shown in FIG. 30.

Information about the grouped inspection region is stored in the inspection region memory area 323.

Figure 31:
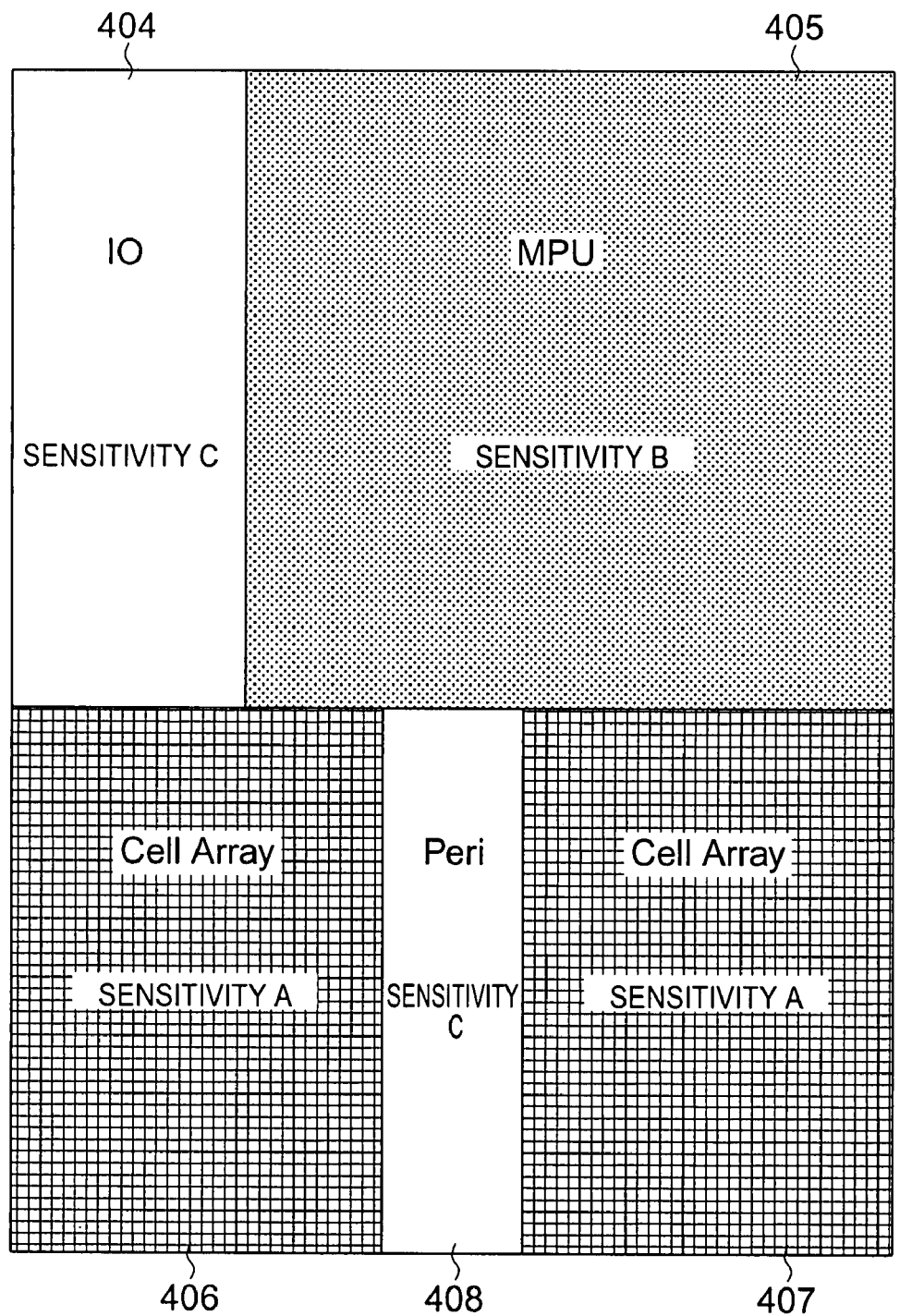
FIG. 31 is a diagram showing an example of sensitivity settings of grouped circuit blocks.

The defect inspecting section 330 sets an inspection parameter (sensitivity) for each group on the basis of the inspection region information. An example of setting of the inspection parameter (sensitivity) is shown in FIG. 31. A sensitivity A-C is set for each group. Then, defect inspections are performed to detect defects. The results of the detection are stored in the defect memory area 324. The coordinates and images of detected defects are displayed on the display 340.

Figure 32:
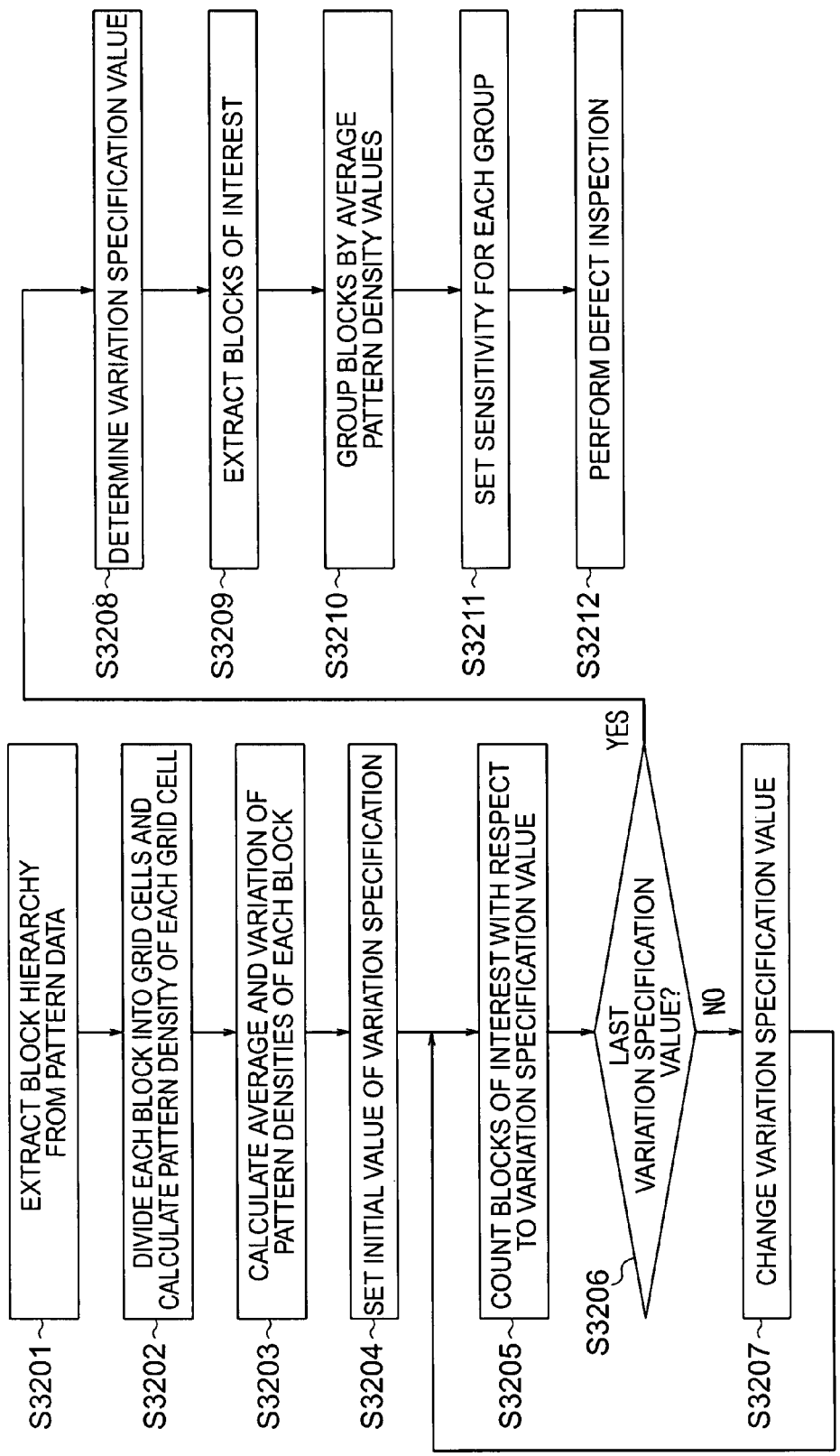
FIG. 32 is a flowchart of a defect inspecting method according to the third embodiment.

A defect inspecting method according to the embodiment will be described with reference to a flowchart shown in FIG. 32.

Step S3201: A block hierarchy is extracted from pattern data (such as GDS).

Step S3202: Each block is divided into grid cells and the pattern density (coverage, edge density, or evaluated sensitivity value) of each grid cell is calculated.

Step S3203: The average value and variation (for example the standard deviation) of the pattern densities of each block are calculated.

Step S3204: The initial variation specification value is set.

Step S3205: Blocks that have pattern density variations less than the variation specification value are counted.

Step S3206: When the last variation specification value is reached, the process proceeds to step S3208; otherwise the process proceeds to step S3207.

Step S3207: The variation specification value is changed by a predetermined amount.

Step S3208: A variation specification value is determined on the basis of the number of blocks having pattern density variations less than the variation specification value and of the maximum number of set blocks.

Step S3209: Blocks having pattern density variations less than the variation specification value determined at step S3208 are extracted.

Step S3210: The blocks extracted at step S3209 are classified into multiple groups on the basis of the average pattern density values.

Step S3211: An inspection parameter (sensitivity) is set for each of the groups created at step S3210 and groups consisting of blocks that have not been extracted at step S3209.

Step S3212: A defect inspection is performed on the basis of the set inspection parameter (sensitivity).

By extracting regions (blocks) that have small pattern density variations, grouping the blocks on the basis of average pattern density values and setting sensitivity for each group in this way, variations in the intensity of reflected inspection light can be reduced and the defect detection rate can be improved Furthermore, regions that reflect more accurately the intensity of reflected inspection light can be extracted and the defect detection rate can be further improved by using, as the pattern densities, edge densities or evaluated sensitivity values instead of coverages.

The defect inspecting apparatus according to the embodiment can be used as the defect inspecting apparatus 104 of the semiconductor device manufacturing system according to the second embodiment described above and shown in FIG. 20.

What is claimed is:

1. A defect inspecting apparatus comprising:
   an inspection region dividing section which divides a defect inspection region of a wafer on which a circuit pattern is formed into a plurality of inspection subregions;
   a pattern density calculating section which calculates the pattern density of each of the inspection subregions on the basis of design data of the circuit pattern;
   an inspection execution region and sensitivity rank setting section which assigns a sensitivity rank to each of the plurality of inspection subregions on the basis of the pattern density, and groups the plurality of inspection subregions which are adjacent to each other and which have the same sensitivity rank to set an inspection execution region; and
   a defect inspecting section which sets an inspection parameter on the basis of sensitivity ranks of the inspection execution regions and inspects the inspection execution regions for a defect.

2. The defect inspecting apparatus according to claim 1, wherein the inspection execution region and sensitivity rank setting section simplifies a shape of the grouped inspection subregions to set the inspection execution region.

3. The defect inspecting apparatus according to claim 1, wherein the inspection region dividing section divides a defect inspection region of the wafer on which the circuit pattern is formed into inspection subregions in a grid pattern.

4. The defect inspecting apparatus according to claim 3, wherein the inspection execution region and sensitivity rank setting section sets the inspection execution regions by:
   assigning a first sensitivity rank or a second sensitivity rank that is higher than the first sensitivity rank;
   creating a first simplified inspection regions in which, if the number of inspection subregions to which the first sensitivity rank is assigned in a row of the grid is less than or equal to "m", the second sensitivity rank is assigned to the inspection subregions, and if the number of inspection subregions to which the first sensitivity rank is assigned in a column of the grid is less than or equal to "n", the second sensitivity rank is assigned to the inspection subregions, where "m" is an integer greater than or equal to 1, "n" is an integer greater than or equal to 1, and "n" is smaller than or equal to "m";

creating a second simplified inspection region in which, if the number of inspection subregions to which the first sensitivity rank is assigned in a column of the grid is less than or equal to "m", the second sensitivity rank is assigned to the inspection subregions, and if the number of inspection subregions to which the first sensitivity rank is assigned in a row of the grid is less than or equal to "n", the second sensitivity rank is assigned to the inspection subregions;

assigning the first sensitivity rank to the inspection subregions to which the first sensitivity rank is assigned in at least one of the first and second simplified inspection regions; and assigning the second sensitivity rank to the inspection subregions to which the first sensitivity rank is not assigned.

5. The defect inspecting apparatus according to claim 2, wherein the pattern density is a line edge density or an evaluated sensitivity value based on a line edge density and a line coverage.

6. The defect inspecting apparatus according to claim 1, wherein the inspection region dividing section extracts information about hierarchy of circuit blocks formed on the wafer from design data of the circuit pattern and divides each of the extracted circuit blocks into inspection subregions in a grid pattern.

7. The defect inspecting apparatus according to claim 6, wherein the inspection execution region and sensitivity rank setting section classifies the circuit blocks into a plurality of groups to set the inspection execution regions on the basis of an average value and a variation of the pattern density of each of the circuit blocks and assigns a sensitivity rank to each of the inspection execution regions.

8. The defect inspecting apparatus according to claim 6, wherein the pattern density is a line coverage or a line edge density, or an evaluated sensitivity value based on a line edge density and line coverage.

9. A defect inspecting method comprising:
dividing a defect inspection region of a wafer on which a circuit pattern is formed into a plurality of inspection subregions;
calculating pattern density of each of the inspection subregions on the basis of design data of the circuit pattern;
assigning a sensitivity rank to each of the plurality of inspection subregions on the basis of the pattern density;
grouping the plurality of the inspection subregions which are adjacent to each other and which have the same sensitivity rank to set an inspection execution region; and
setting an inspection parameter on the basis of sensitivity ranks of the inspection execution regions and inspecting the inspection execution regions for a defect.

10. The defect inspecting method according to claim 9, wherein a shape of the grouped inspection subregions is simplified to set the inspection execution region.

11. The defect inspecting method according to claim 9, wherein a defect inspection region of the wafer on which the circuit pattern is formed is divided into inspection subregions in a grid pattern.

12. The defect inspecting method according to claim 11, wherein the inspection execution regions is set by:

assigning as the sensitivity rank a first sensitivity rank or a second sensitivity rank that is higher than the first sensitivity rank;

creating a first simplified inspection regions in which, if the number of inspection subregions to which the first sensitivity rank is assigned in a row of the grid in the group is less than or equal to "m", the second sensitivity rank is assigned to the inspection subregions, and if the number of inspection subregions to which the first sensitivity rank is assigned in a column of the grid is less than or equal to "n", the second sensitivity rank is assigned to the inspection subregions, where "m" is an integer greater than or equal to 1, "n" is an integer greater than or equal to 1, and "n" is smaller than or equal to "m";

creating a second simplified inspection region in which, if the number of inspection subregions to which the first sensitivity rank is assigned in a column of the grid in the group is less than or equal to "m", the second sensitivity rank is assigned to the inspection subregions, and if the number of inspection subregions to which the first sensitivity rank is assigned in a row of the grid is less than or equal to "n", the second sensitivity rank is assigned to the inspection subregions;

assigning the first sensitivity rank to the inspection subregions to which the first sensitivity rank is assigned in at least one of the first and second simplified inspection regions; and assigning the second sensitivity rank to the inspection subregions to which the first sensitivity rank is not assigned.

13. The defect inspecting method according to claim 10, wherein a line edge density or an evaluated sensitivity value based on a line edge density and a line coverage is calculated as the pattern density.

14. The defect inspecting method according to claim 9, wherein information about hierarchy of circuit blocks formed on the wafer is extracted from design data of the circuit pattern and each of the extracted circuit blocks is divided into inspection subregions in a grid pattern.

15. The defect inspecting method according to claim 14, the circuit blocks are classified into a plurality of groups to set the inspection execution regions on the basis of an average value and a variation of the pattern density of each of the circuit blocks and a sensitivity rank is assigned to each of the inspection execution regions.

16. The defect inspecting method according to claim 14, wherein a line coverage or a line edge density, or an evaluated sensitivity value based on a line edge density and a line coverage is calculated as the pattern density.

17. A semiconductor apparatus manufacturing system comprising:
a patterning apparatus which forms a circuit pattern on a wafer in accordance with an equipment parameter;
a defect inspecting apparatus comprising an inspection region dividing section which divides a defect inspection region of the wafer on which the circuit pattern is formed into a plurality of inspection subregions, a pattern density calculating section which calculates the pattern density of each of the inspection subregions on the basis of design data of the circuit pattern, an inspection execution region and sensitivity rank setting section which assigns a sensitivity rank based on the pattern density to a plurality of inspection execution regions, each including a plurality of the inspection subregions, and a defect inspecting section which sets an inspection parameter on the basis of sensitivity ranks of the inspection execution regions, inspects the inspection execution regions for a defect, and outputs the result of the inspection; and an equipment parameter controller which generates correction information for the equipment parameter on the basis of the result of the inspection and outputs the correction information to the patterning apparatus.

18. The semiconductor apparatus manufacturing system according to claim 17, wherein the inspection region dividing section divides a defect inspection region of the wafer on which the circuit pattern is formed into inspection subregions in a grid pattern;

the pattern density calculating section calculates as the pattern density a line edge density, or an evaluated sensitivity value based on a line edge density and a line coverage; and the inspection execution region and sensitivity rank setting section assigns a sensitivity rank to each of the inspection subregions on the basis of the pattern density, groups a plurality of the inspection subregions adjacent to each other and to which the same sensitivity rank is assigned, and simplifies the shape of the grouped inspection subregions to set the inspection execution region.

19. The semiconductor apparatus manufacturing system according to claim 17, wherein the inspection region dividing section extracts information about hierarchy of circuit blocks formed on the wafer from design data of the circuit pattern and divides each of the extracted circuit blocks into inspection subregions in a grid pattern;

the pattern density calculating section calculates as the pattern density a line coverage, or a line edge density, or an evaluated sensitivity value based on a line edge density and a line coverage; and the inspection execution region and sensitivity rank setting section classifies the circuit blocks into a plurality of groups to set the inspection execution regions on the basis of an average value and a variation of the pattern density of each of the circuit blocks and assigns a sensitivity rank to each of the inspection execution regions.

20. A semiconductor apparatus manufacturing method comprising:

forming a circuit pattern on a wafer in accordance with an equipment parameter;

dividing a defect inspection region of the wafer on which the circuit pattern is formed into a plurality of inspection subregions;

calculating the pattern density of each of the inspection subregions on the basis of design data of the circuit pattern;

assigning a sensitivity rank based on the pattern density to a plurality of inspection execution regions, each including a plurality of the inspection subregions;

setting an inspection parameter on the basis of sensitivity ranks of the inspection execution regions and performing defect inspection on the inspection execution regions;

correcting the equipment parameter on the basis of the result of the defect inspection; and forming a circuit pattern on a wafer in accordance with the corrected equipment parameter.

* * * * *